(12) United States Patent
Turner

(10) Patent No.: US 7,224,769 B2
(45) Date of Patent: May 29, 2007

(54) DIGITAL X-RAY CAMERA

(75) Inventor: D. Clark Turner, Payson, UT (US)

(73) Assignee: Aribex, Inc., Orem, UT (US)

( * ) Notice: Subject to any disclaimer, the term of this patent is extended or adjusted under 35 U.S.C. 154(b) by 0 days.

(21) Appl. No.: 10/529,806

(22) PCT Filed: Mar. 21, 2005

(86) PCT No.: PCT/US2005/005454

§ 371 (c)(1),
(2), (4) Date: Aug. 1, 2005

(87) PCT Pub. No.: WO2006/101468

PCT Pub. Date: Sep. 28, 2006

(65) Prior Publication Data

US 2006/0098779 A1    May 11, 2006

Related U.S. Application Data

(60) Provisional application No. 60/546,575, filed on Feb. 20, 2004.

(51) Int. Cl.
*H05G 1/64* (2006.01)
*H05G 1/06* (2006.01)
*H05G 1/10* (2006.01)

(52) U.S. Cl. .................. 378/98.2; 378/98; 378/102

(58) Field of Classification Search .............. 378/98, 378/98.2, 98.8, 101–104, 191, 109–112
See application file for complete search history.

(56) References Cited

U.S. PATENT DOCUMENTS

| | | | |
|---|---|---|---|
| 2,063,329 A * | 12/1936 | Morrison | ............ 378/203 |
| 3,728,457 A | 4/1973 | Lundin | |
| 3,828,194 A | 8/1974 | Grasser | |
| 3,925,672 A | 12/1975 | Soder et al. | |
| 4,039,811 A | 8/1977 | Ennslin et al. | |
| 4,170,735 A * | 10/1979 | Codina et al. | ............ 378/96 |
| 4,191,889 A | 3/1980 | Cowell | |
| 4,221,969 A | 9/1980 | Schmidt | |

(Continued)

FOREIGN PATENT DOCUMENTS

EP    0247758    12/1987

(Continued)

OTHER PUBLICATIONS

U.S. Appl. No. 10/529,805, filed Mar. 30, 2005, Turner, Clark.

(Continued)

*Primary Examiner*—Edward J. Glick
*Assistant Examiner*—Anastasia S. Midkiff
(74) *Attorney, Agent, or Firm*—Kenneth E. Horton; Kirton & McConkie

(57) ABSTRACT

Portable x-ray devices and methods for using such devices are described. The devices have an x-ray tube powered by an integrated power system. The x-ray tube is shielded with a low-density insulating material containing a high-Z substance. The devices can also have an integrated display component. With these components, the size and weight of the x-ray devices can be reduced and the portability of the devices enhanced. The x-ray devices also have an x-ray detecting means that is not structurally attached to the device and therefore is free standing. Consequently, the x-ray devices can also be used as a digital x-ray camera. The portable x-ray devices are especially useful for applications where portability is an important feature such as in field work, remote operations, and mobile operations such as nursing homes, home healthcare, or teaching classrooms. This portability feature can be particularly useful in multi-suite medical and dental offices where a single x-ray device can be used as a digital x-ray camera in multiple offices instead of requiring a separate device in every office.

33 Claims, 17 Drawing Sheets

U.S. PATENT DOCUMENTS

| | | | |
|---|---|---|---|
| 4,311,913 A | 1/1982 | Resnick et al. | |
| 4,490,834 A | 12/1984 | Sudani | |
| 4,646,338 A * | 2/1987 | Skillicorn | 378/110 |
| 4,694,480 A | 9/1987 | Skillicorn | |
| 4,768,216 A | 8/1988 | Harvey et al. | |
| 4,775,992 A | 10/1988 | Resnick et al. | |
| 4,797,907 A | 1/1989 | Anderton | |
| 4,809,311 A | 2/1989 | Arai et al. | |
| 4,811,375 A | 3/1989 | Klostermann | |
| 4,840,471 A * | 6/1989 | Mitani et al. | 359/722 |
| 4,856,036 A | 8/1989 | Malcolm et al. | |
| 4,930,146 A | 5/1990 | Flakas et al. | |
| 4,979,198 A * | 12/1990 | Malcolm et al. | 378/102 |
| 5,077,771 A * | 12/1991 | Skillicorn et al. | 378/102 |
| 5,111,493 A | 5/1992 | Siedband | |
| 5,153,900 A | 10/1992 | Nomikos et al. | |
| 5,166,965 A * | 11/1992 | Collier | 378/101 |
| 5,379,335 A | 1/1995 | Griesmer et al. | |
| 5,514,873 A * | 5/1996 | Schulze-Ganzlin et al. | 250/394 |
| 5,631,943 A | 5/1997 | Miles | |
| 5,708,694 A | 1/1998 | Beyerlein et al. | |
| 5,909,478 A * | 6/1999 | Polichar et al. | 378/98.2 |
| 6,038,287 A | 3/2000 | Miles | |
| 6,205,200 B1 | 3/2001 | Boyer et al. | |
| 6,327,338 B1 | 12/2001 | Golovanivsky et al. | |
| 6,459,767 B1 | 10/2002 | Boyer | |
| 6,661,876 B2 | 12/2003 | Turner et al. | |
| 2003/0002627 A1 | 1/2003 | Espinosa et al. | |
| 2003/0048877 A1 | 3/2003 | Price et al. | |
| 2003/0142788 A1 | 7/2003 | Cho et al. | |
| 2004/0146142 A1* | 7/2004 | Maijala | 378/102 |
| 2005/0018817 A1* | 1/2005 | Oettinger et al. | 378/203 |
| 2005/0053199 A1 | 3/2005 | Miles | |
| 2005/0213709 A1 | 9/2005 | Dinsmore et al. | |

FOREIGN PATENT DOCUMENTS

| | | |
|---|---|---|
| EP | 0488991 | 6/1992 |
| EP | 0524064 | 1/1993 |
| EP | 0784965 | 7/1997 |
| JP | 59-073897 | 4/1984 |
| JP | 62-246300 | 10/1987 |
| JP | 62-283600 | 12/1987 |
| JP | 03-225797 | 10/1991 |
| WO | WO 92-04727 | 3/1992 |
| WO | WO 95-20241 | 7/1995 |
| WO | WO 96-05600 | 2/1996 |
| WO | WO 2004047504 | 6/2004 |
| WO | WO 200508195 | 1/2005 |
| WO | WO 2005/005454 | 2/2005 |
| WO | WO 2005/081956 | 9/2005 |
| WO | WO 2006/065035 A1 | 6/2006 |

OTHER PUBLICATIONS

Fiorini, C.; Longoni, A.; Milazzo, M.; Zaraga, F, *In-situ, non-destructive identification of chemical elements by means of portable EDXRF spectrometer*. Nuclear Science Symposium, 1998. Conference Record. 1998 IEEE, vol. 1, Iss., 1998, pp. 375-380, vol. 1 (Abstract).

Mesyats, G.A.; Shpak, V.G.; Yalandin, M.I.; Shunailov, S.A. *RADAN-Expert portable high-current accelerator*, Pulsed Power Conference, 1995. Digest of Technical Papers. Tenth IEEE International, vol. 1, Iss., Jul. 3-6, 1995, pp. 539-543 vol. 1 (Abstract).

Fiorini, C.; Longoni, A. *In-situ, non-destructive identification of chemical elements by means of portable EDXRF spectrometer*, Nuclear Science, IEEE Transactions on, vol. 46, Iss.6, Dec. 1999 pp. 2011-2016 (Abstract).

Bertolucci, E.; Boerkamp, T.; Maiorino, M.; Mettivier, G.; Montesi, M.C.; Russo, P. *Portable system for imaging of /spl alpha/, and X-ray sources with silicon pixel detectors and Medipix1 readout*, Nuclear Science, IEEE Transactions on, vol. 49, Iss.4, Aug. 2002 pp. 1845-1850 (Abstract).

Mesyats, G.A.; Korovin, S.D.; Rostov, V.V.; Shpak, V.G.; Yalandin, M.I., *The RADAN series of compact pulsed power Generators and their applications*, Proceedings of the IEEE, vol. 92, Iss.7, Jul. 2004 pp. 1166-1179 (Abstract).

Kastis, G.A.; Furenlid, L.R.; Wilson, D.W.; Peterson, T.E.; Barber, H.B.; Barrett, H.H., *Compact CT/SPECT small-animal imaging system*, Nuclear Science, IEEE Transactions on, vol. 51, Iss.1, Feb. 2004 pp. 63-67 (Abstract).

Shrivastava, P.; O'Connell, S.; Whitley, A., *Handheld x-ray fluorescence: practical application as a screening tool to detect the presence of environmentally-sensitive substances in electronic equipment*, Electronics and the Environment, 2005. Proceedings of the 2005 IEEE International Symposium on, vol., Iss., May 16-19, 2005 pp. 157-162 (Abstract).

Idrissi, M.M.; Dudemaine, M.; Viladrosa, R.; Robert, E.; Cachoncinlle, C.; Pouvesle, J.M., *Experimental study and development of a single focus burst X-ray flash*, Pulsed Power Conference, 2003. Digest of Technical Papers. PPC-2003. 14th IEEE International, vol. 2, Iss., Jun. 15-18, 2003 pp. 752-755 vol. 2 (Abstract).

Maur, F., *X-ray inspection for electronic packaging latest developments*, Electronic Packaging Technology Proceedings, 2003. ICEPT 2003. Fifth International Conference on, vol., Iss., Oct. 28-30, 2003 pp. 235-239 (Abstract).

Matsumoto, T.; Mimura, H., *X-ray radiography system using graphite-nanofibers cold cathode*, Vacuum Microelectronics Conference, 2003. Technical Digest of the 16th International, vol., Iss., Jul. 7-11, 2003 pp. 301-302 (Abstract).

Kastis, G.A.; Furenlid, L.R.; Wilson, D.w.; Peterson, T.E.; Barber, H.B.; Barrett, H.H., *Compact CT/SPECT small-animal imaging system* Nuclear Science Symposium Conference Record, 2002 IEEE, vol. 2, Iss., Nov. 10-16, 2002 pp. 797-801 vol. 2 (Abstract).

Bertolucci, E.; Boerkamp, T.; Maiorino, M.; Mettivier, G.; Montesi, M.C.; Russo, P., *Portable system for imaging of /spl alpha/, /spl beta/ and X-ray sources with silicon pixel detectors and Medipix 1 read out*, Nuclear Science Symposium Conference Record, 2001 IEEE, vol. 2, Iss., Nov. 4-10, 2001 pp. 709-713 vol. 2 (Abstract).

Longoni, A.; Fiorini, C.; Guazzoni, C.; Gianoncelli, A.; Struder, L.; Soltau, H.; Lechner, P.; Bjeoumikhov, A.; Schmalz, J.; Langhoff, N.; Wedell, R.; Kolarik, V., *A new XRF spectrometer based on a ring-shaped multi-element Silicon Drift Detector and on X-ray capillary optics*, Nuclear Science Symposium Conference Record, 2001 IEEE, vol. 2, Iss., Nov. 4-10, 2001, pp. 897-901 vol. 2 (Abstract).

Shirochin, L.A.; Fursey, G.N., *High-power soft X-ray tube with an explosive emission cathode*, Discharges and Electrical Insulation in Vacuum, 1998. Proceedings ISDEIV. XVIIIth International Symposium on, vol. 2, Iss., Aug. 17-21, 1998, pp. 672-674 vol. 2 (Abstract).

Fursey, G.N.; Shirochin, L.A., *Explosive emission phenomenon and portable X-ray tubes*, Vacuum Microelectronics Conference, 1998. Eleventh International, vol., Iss., Jul. 19-24, 1998, pp. 142-143 (Abstract).

Takano, H.; Hatekeyama, T.; Sun, J.M.; Laknath, K.G.D.; Nakaoka, M., *Feasible characteristic evaluations of resonant PWM inverter-linked DC—DC power converter using high-voltage transformer parasitic circuit components*, Power Electronics and Variable Speed Drives, 1996. Sixth International Conference on (Conf. Publ. No. 429), vol., Iss., Sep. 23-25, 1996 pp. 525-533.

Shirouzu, S.; Inoue, S., *A new type X-ray instant camera*, Nuclear Science, IEEE Transactions on, vol. 39, Iss.5, Oct. 1992 pp. 1528-1531 (Abstract).

Sudarkin, A.N.; Ivanov, O.P.; Stepanov, V.E.; Volkovich, A.G.; Turin, A.S.; Danilovich, A.S.; Rybakov, D.D.; Urutskoev, L.I., *High-energy radiation visualizer (HERV): a new system for imaging in X-ray and gamma-ray emission regions*, Nuclear Science, IEEE Transactions on, vol. 43, Iss.4, Aug. 1996, pp. 2427-2433 (Abstract).

Longoni, A.; Fiorini, C.; Guazzoni, C.; Gianoncelli, A.; Struder, L.; Soltau, H.; Lechner, P.; Bjeoumikhov, A.; Schmalz, J.; Langhoff, N.; Wedell, R., *A new XRF Spectrometer based on a ring-shaped*

*multi-element silicon drift detector and on X-ray capillary optics*, Nuclear Science, IEEE Transactions on, vol. 49, Iss.3, Jun. 2002, pp. 1001-1005 (Abstract).

Sinha, N.; Yeow, J.T.-W., *Carbon nanotubes for biomedical applications*, NanoBioscience, IEEE Transactions on, vol. 4, Iss.2, Jun. 2005, pp. 180-195 (Abstract).

Kidd, R.; Rabinowitz, P.; Garrison, L.; Meyer, A.; Adamson, A.; Auroux, C.; Baldauf, J.; Clement, B.; Palmer, A.; Taylor, E.; Graham, A., *The Ocen Drilling Program III: The shipboard laboratories on "JOIDES Resolution"*, OCEANS, vol. 17, Iss., Nov. 1985, pp. 133-145 (Abstract).

Chuvatin, A.S.; Rudakov, L.I.; Velikovich, A.L.; Davis, J.; Oreshkin, V.I., *Heating of on-axis plasma heating for keV X-ray production with Z-pinches*, Plasma Science, IEEE Transactions on, vol. 33, Iss.2, Apr. 2005, pp. 739-751 (Abstract).

Borisov et al., *Ultrabright Multikilovolt Coherent Tunable X-Ray Source at~2.71 —2.93 Å for Biological Microimaging*, 2004, American Institute of Physics 0-7354-0195-0. (Abstract).

Momose et al., *X-Ray Talbot Interferometry for Medical Phase Imaging*, 2004 American Institute of Physics 0-7354-0195-0 (Abstract).

Sasaki et al., *Protein Crystallography Beam Line at MIRRORCLE*, 2004 American Institute of Physics 0-7354-0195-0. (Abstract).

Hirai, *Novel Edge-Enhanced X-Ray Imaging Utilizing MIRRORCLE*, 2004 American Institute of Physics 0-7354-0195-0. (Abstract).

Hironari Yamada, *Features of the portable synchrotrons named MIRRORCLE*, 2004 American Institute of Physics 0-7354-0195-0. (Abstract).

Hironari Yamada, *The Synchrotron Light Life Science Center Granted by the MEXT 21st Century COE Program*, 2004 American Institute of Physics 0-7354-0195-0. (Abstract).

Hirai et al., *Novel Edge-Enhanced X-ray Imaging by MIRRORCLE*, 2004 American Institute of Physics 0-7354-0195-0.

Yue et al., *Generation of continuous and pulsed diagnostic imaging x-ray radiation using a carbon-nanotube-based field-emission cathode*, Applied Physics Letters, vol. 81, No. 2, Jul. 8, 2002. (Abstract).

Moreno et al., *Small-Chamber 4.7 kj Plasma Focus for Applications*, 2001 American Institute of Physics 1-56396-999-Aug. 2001 (Abstract).

Boyer et al., *Portable hard x-ray source for nondestructive testing and medical imaging*, Review of Scientific Instruments vol. 69, No. 6, Jun. 1998. (Abstract).

Mikerov et al., *Prospects of fast neutron radiography based on portable neutron generators*, Proc. SPIE vol. 4142, p. 74-80, Penetrating Radiation Systems and Applications II, Dec. 2000. (Abstract).

Fry et al., *Recent developments in electronic radiography at Los Alamos*, Proc. SPIE vol. 3769, p. 111-123, Penetrating Radiation Systems and Applications, Oct. 1999. (Abstract).

Smith, et al., *Evaluation of a CMOS image detector for low-cost and power medical x-ray imaging applications*, Proc. SPIE vol. 3659, p. 952-961, Medical Imaging 1999, May 1999. (Abstract).

Spartiotis et al., *Novel direct digital modular x-ray device and system*, Proc. SPIE vol. 3336, p. 529-536, Medical Imaging 1998, Jul. 1998. (Abstract).

Boyer et al., *Pulsed hard x-ray source for nondestructive testing and medical imaging*, Proc. SPIE vol. 3154, p. 16-26, Coherent Electron-Beam X-Ray Sources: Techniques and Applications, Oct. 1997. (Abstract).

Xiang et al., *New type of x-ray-wafer image intensifier with CsI-CsI/MCP photocathodes: its design and assessment*, Proc. SPIE vol. 1982, p. 230-235, Photoelectronic Detection and Imaging: Technology and Applications '93, Apr. 1993. (Abstract).

Kutlubay et al., *Cost-effective, high-resolution, portable digital x-ray imager*, Proc. SPIE vol. 2432, p. 554-562, Medical Imaging 1995, May 1995. (Abstract).

Seely et al., *Dual-Energy Bone Densitometry Using a Single 100 NSX—Ray Pulse Medical Physics*, vol. 25, Oct. 1998 (Abstract).

Piorek, Stanislaw, *Field-Portable X-Ray Fluorescence Spectrometry: Past, Present, and Future*, Metorex, Inc., Princeton, New Jersey, Mar. 1997. (Abstract).

"DentalEz Portable HDX Intraoral X-ray," User's Manual, Flow X-ray Inc., Mar. 2000 (Abstract).

Stumbo et al., *Direct Analysis of Molybdenum Target Generated X-ray Spectra with a Portable Device*, Medical Physics, Oct. 2004, vol. 31 Issue 10, pp. 2763-2770.

Wang et al., *Fast Reconstruction for Uncontained Cone-Beam Tomosynthesis*, Proceedings of SPIE, May 2004, vol. 5368, pp. 930-938 (Abstract).

Alexander Sasov, *Desktop X-Ray Micro-CT Instruments*, Proceedings of SPIE, Jan. 2002, vol. 4053, pp. 282-290 (Abstract).

Schewe et al., *A Room-Based Diagnostic Imaging System for Measurement of Patient Setup*, Medical Physics, Dec. 1998, vol. 25, Issue 12, pp. 2385-2387.

\* cited by examiner

DIGITAL X-RAY CAMERA

CROSS-REFERENCE TO RELATED APPLICATION

This application claims priority of U.S. patent application Ser. No. 60/546,575, filed on Feb. 20, 2004, the entire disclosure of which is incorporated herein by reference.

FIELD OF THE INVENTION

The invention generally relates to x-ray devices and methods for using the same. More particularly, the invention relates to portable x-ray devices that contain an unattached x-ray detector, methods for using such portable x-ray devices as a digital x-ray camera, and systems containing such portable x-ray devices.

BACKGROUND OF THE INVENTION

Typical x-ray tubes and x-ray devices (device containing x-ray tubes) have been known and used for some time. Unfortunately, they are usually bulky and are powered by heavy, high-voltage power supplies that restrict mobility. As well, they are often difficult and time-consuming to use. In many instances, a sample for analysis must be sent to an off-site laboratory for analysis by the x-ray device.

These limitations can be very inconvenient for many popular uses of x-ray devices containing them. Such uses include x-ray fluorescence (XRF) of soil, water, metals, ores, well bores, etc., as well as diffraction and plating thickness measurements. Typical x-ray imaging applications require the sample to be imaged to be brought to the x-ray device. These limitations have led to an increased interest in making x-ray devices portable. See, for example, U.S. Pat. Nos. 6,661,876, 6,459,767, 6,038,287, and 6,205,200; U.S. Published Patent Applications 2003/0048877, 2003/0002627, and 2003/0142788; and European Patent Nos. EP0946082, EP0524064, EP0247758, EP0784965, and EP0488991; the entire disclosures of which are incorporated herein by reference.

Many of these existing designs increase the portability of x-ray devices. At the same time, however, these designs are limited for several reasons. First, most of the designs are not truly portable since they have an external power source (i.e., require utility-supplied line voltage). Second, while some of the portable designs, especially the XRF systems, have internal or "integrated" power supplies, they don't have the high x-ray tube current load that is often necessary for x-ray imaging. For example, energy-dispersive XRF typically requires x-ray beam currents of less than 1 milliampere while x-ray imaging typically requires greater than about 2 milliamperes. Finally, the radiation shielding for the x-ray tubes usually comprises lead, which is quite heavy and limits the portability of the device.

A further limitation on design of the increased portability is the image display components. High-quality imaging displays for displaying the results of the x-ray analysis are difficult to integrate into the design of the housing of the portable x-ray device. Consequently, many of the portable designs have the image display component external to the chassis or housing containing the x-ray tube.

SUMMARY OF THE INVENTION

The invention relates to portable x-ray devices and methods for using such devices. The x-ray devices have an x-ray tube powered by an integrated power system. The x-ray tube is shielded with a low-density insulating material containing a high-Z substance. The x-ray devices can also have an integrated display component. With these components, the size and weight of the x-ray devices can be reduced and the portability of the devices enhanced. The x-ray devices can also have detecting means that is not structurally attached to the device and therefore is free standing. Consequently, the x-ray devices can also be used as a digital x-ray camera. The portable x-ray devices are especially useful for applications where portability is an important feature such as in field work, remote operations, and mobile operations such as nursing homes, home healthcare, or teaching classrooms. This portability feature can be particularly useful in multi-suite medical and dental offices where a single x-ray device can be used as a digital x-ray camera in multiple offices instead of requiring a separate device in every office.

BRIEF DESCRIPTION OF THE DRAWINGS

The following description of the invention can be understood in light of the Figures, in which:

FIGS. 1-17 illustrate specific aspects of the invention and are a part of the specification.

In the Figures, the thickness and configuration of components may be exaggerated for clarity. The same reference numerals in different drawings represent the same component. Together with the following description, the Figures demonstrate and explain the principles of the invention.

DETAILED DESCRIPTION OF THE INVENTION

The following description provides specific details in order to provide a thorough understanding of the invention. The skilled artisan, however, would understand that the invention can be practiced without employing these specific details. Indeed, the invention can be practiced by modifying the illustrated method and resulting product and can be used in conjunction with apparatus and techniques conventionally used in the industry. While the invention is described for use in x-ray imaging for dental purposes, it could be used in other medical applications such as medical imaging, veterinary, and bone densitometry. As well, it could be used for non-dental and non-medical applications such as industrial imaging, metal fatigue inspections, weld-inspection for cracks/voids and pipes, for security inspections allowing random inspection of parcels and carry-on baggage, and the like.

As described above, the invention includes a portable x-ray device that is used primarily for remote and/or office applications, including in multi-suite office locations. The x-ray device can be designed to be either handheld or temporarily fixed to a given location, such as a tripod-mount operation. As well, the invention could be mounted on any other semi-stable apparatus, such as an articulating arm or C-arm as commonly used in radiology applications and described in the publications mentioned above.

The x-ray device of the invention is portable in that it can be transported by hand carrying it from one location to a second location without support by any mechanical apparatus. Because it uses an integrated power system, the location of its use can be independent of any external fixed power source, such as utility-supplied AC voltage often required in the home or office. As well, the x-ray device contains detecting means that is not structurally attached to the device and therefore is free standing. This independence from an external power source and free-standing detecting means are particularly useful features of the x-ray devices of the invention.

Figure 1:
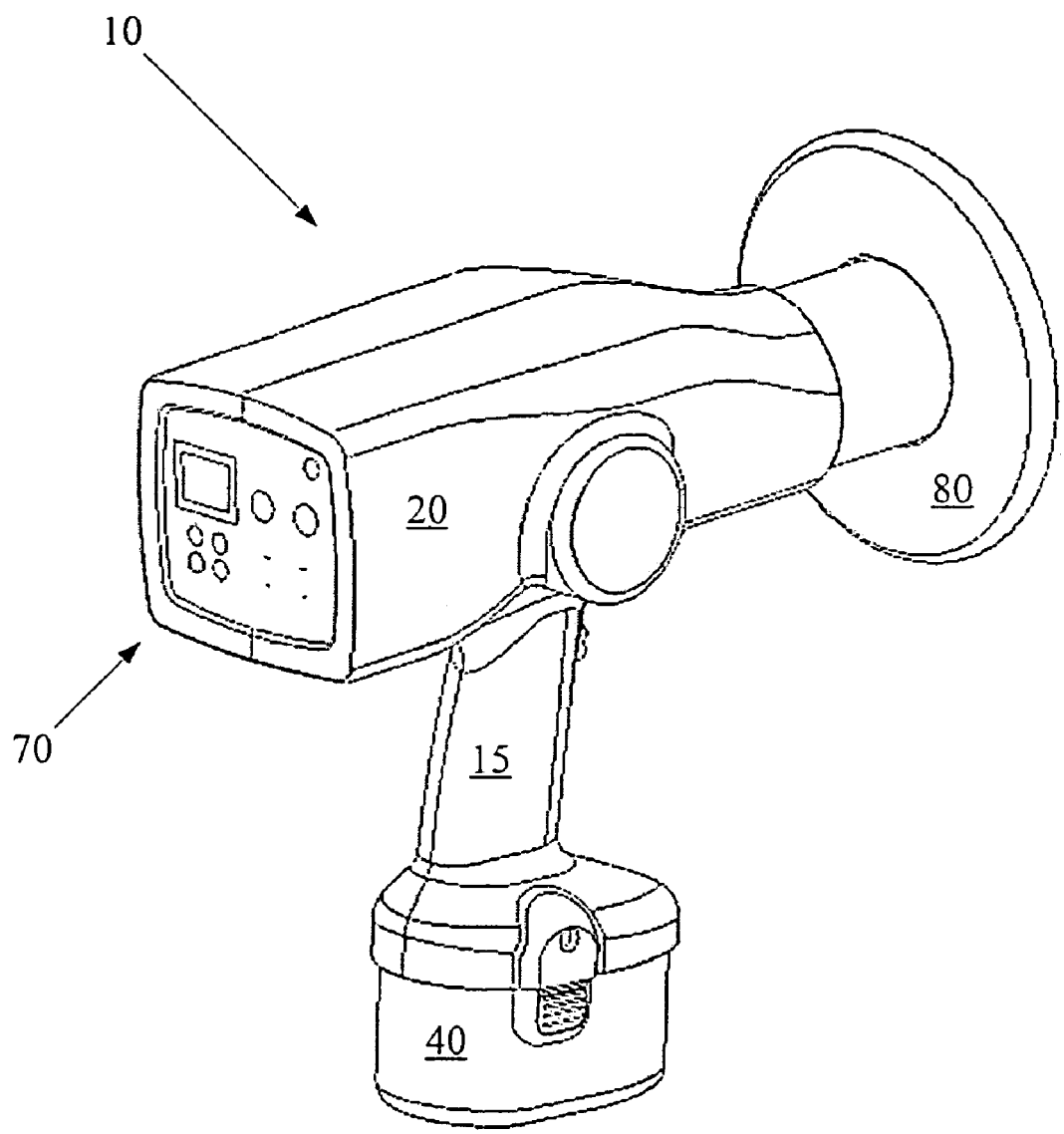
FIGS. 1-2 depict the x-ray device in one aspect of the invention.
Figure 2:
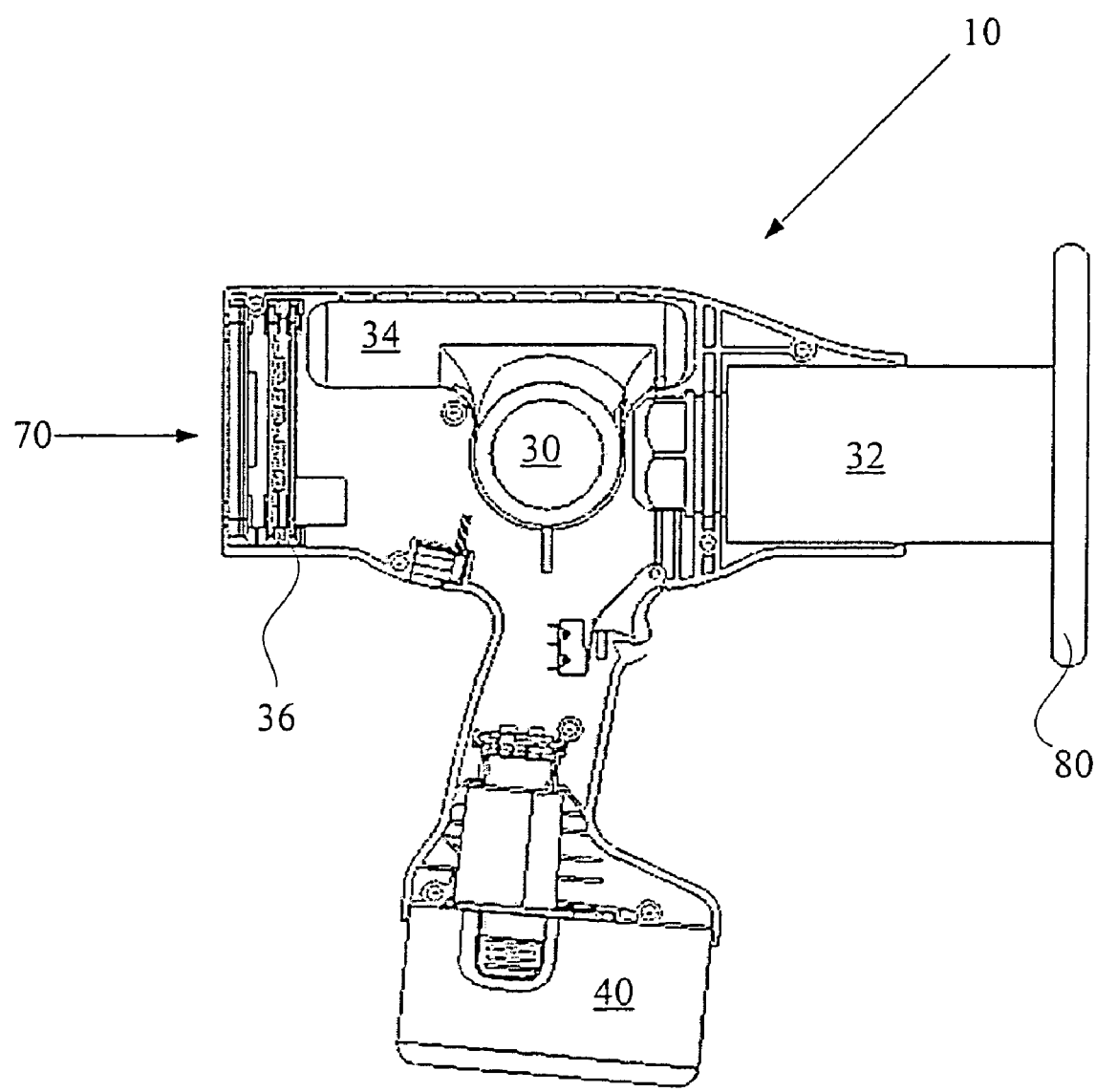
Figure 4:
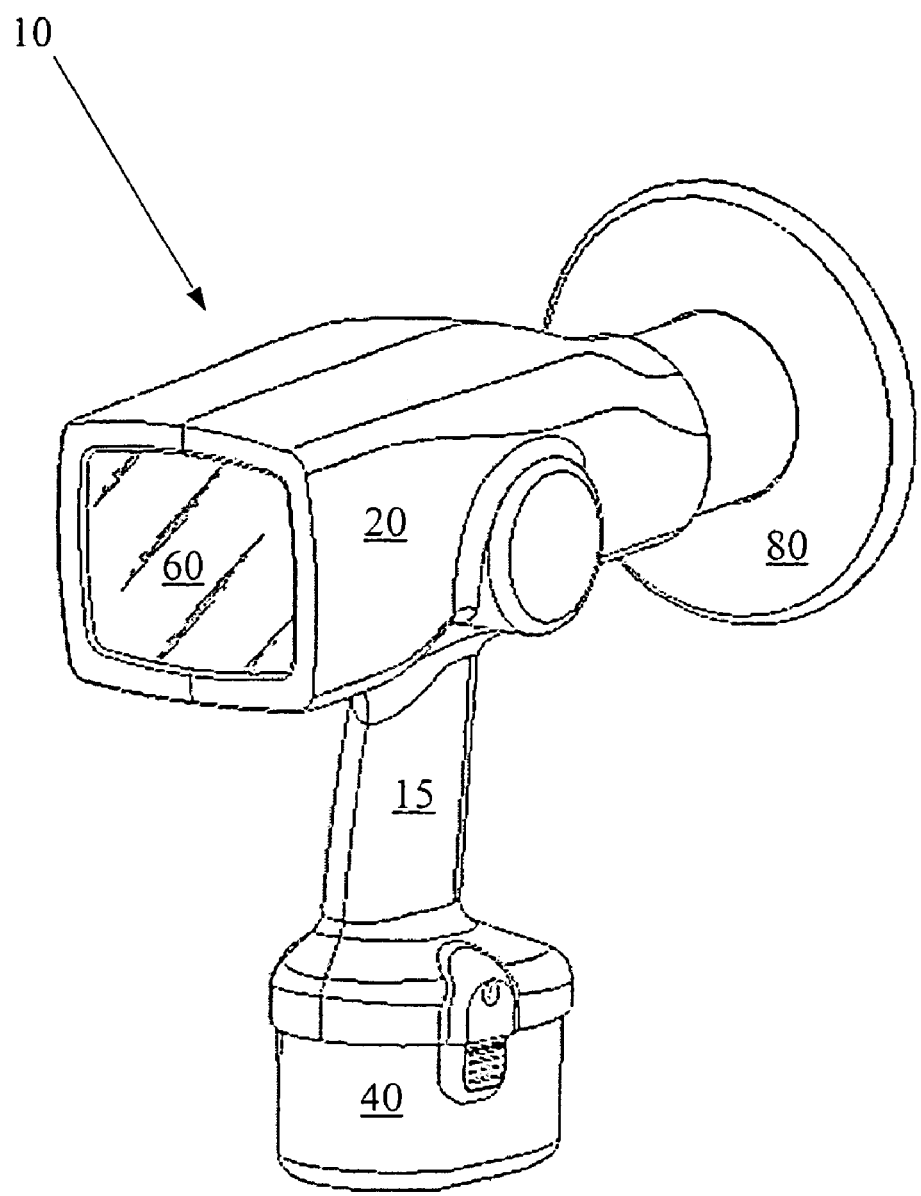
FIG. 4 depicts the x-ray device in another aspect of the invention.

In the aspect of the invention shown in FIGS. 1-2, the x-ray device 10 of the invention contains a housing or chassis 20 to contain all the internal components of the device. The housing 20 encloses an x-ray tube 30 for producing the x-rays. The x-ray device 10 contains a power system (including power source 40) to provide power for the device 10 and means for detecting the x-rays, such as film, CCD sensors, or imaging plates (not shown). The x-ray device 10 also contains means for displaying the results of the analysis such as an integrated image display screen 60 (shown in FIG. 4); control means such as controller 70; and radiation shielding 80 to shield the operator of the device from backscattered radiation from the sample.

The x-ray device 10 also contains any other components known in the art for efficient operation (such as x-ray collimator 32), including those components described in the documents mentioned above.

The x-ray device 10 contains a unique system for providing power to the x-ray device. The power system of the x-ray device comprises a power source 40, power supply 34, and conversion means. The power source 40 used in the x-ray device of the invention can be any known in the art that can supply the desired amount of power, yet fit within the space limitations of the x-ray device. In one aspect of the invention, the power source comprises a battery, such as a 14.4V NiCd battery pack. The power source can be recharged by any suitable means, such as by connection to an appropriate voltage when using batteries that are rechargeable.

Figure 6:
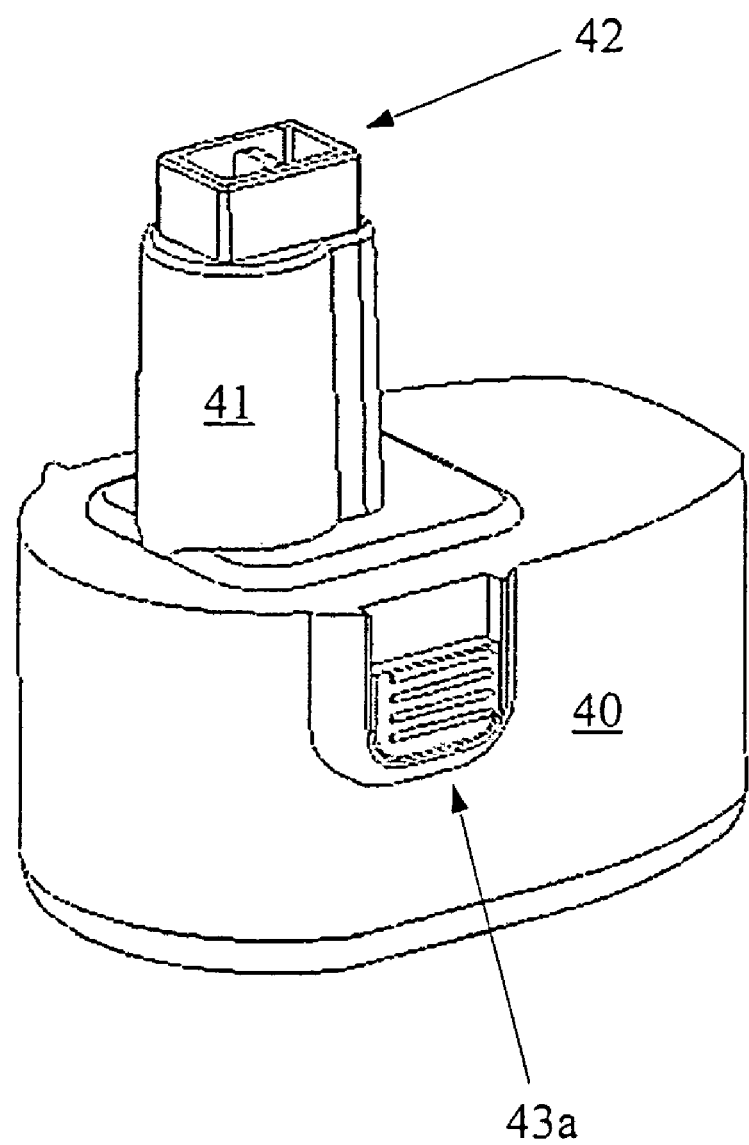
FIGS. 6-7 depict the power source of the x-ray device and method for connecting the power source to the x-ray device in one aspect of the invention.

In one aspect of the invention, the power source 40 is removable from the remainder of the x-ray device 10. In this aspect of the invention, the power source 40 comprises mechanical and electrical means for connecting the power source 40 to the x-ray device 10. The electrical and mechanical connection means can be any of those known in the art. As depicted in FIG. 6, the electrical connection means can comprise an extension member 41 with an electrical connector 42 contained in an upper portion thereof. The mechanical connection means comprises a release mechanism 43a.

Figure 7:
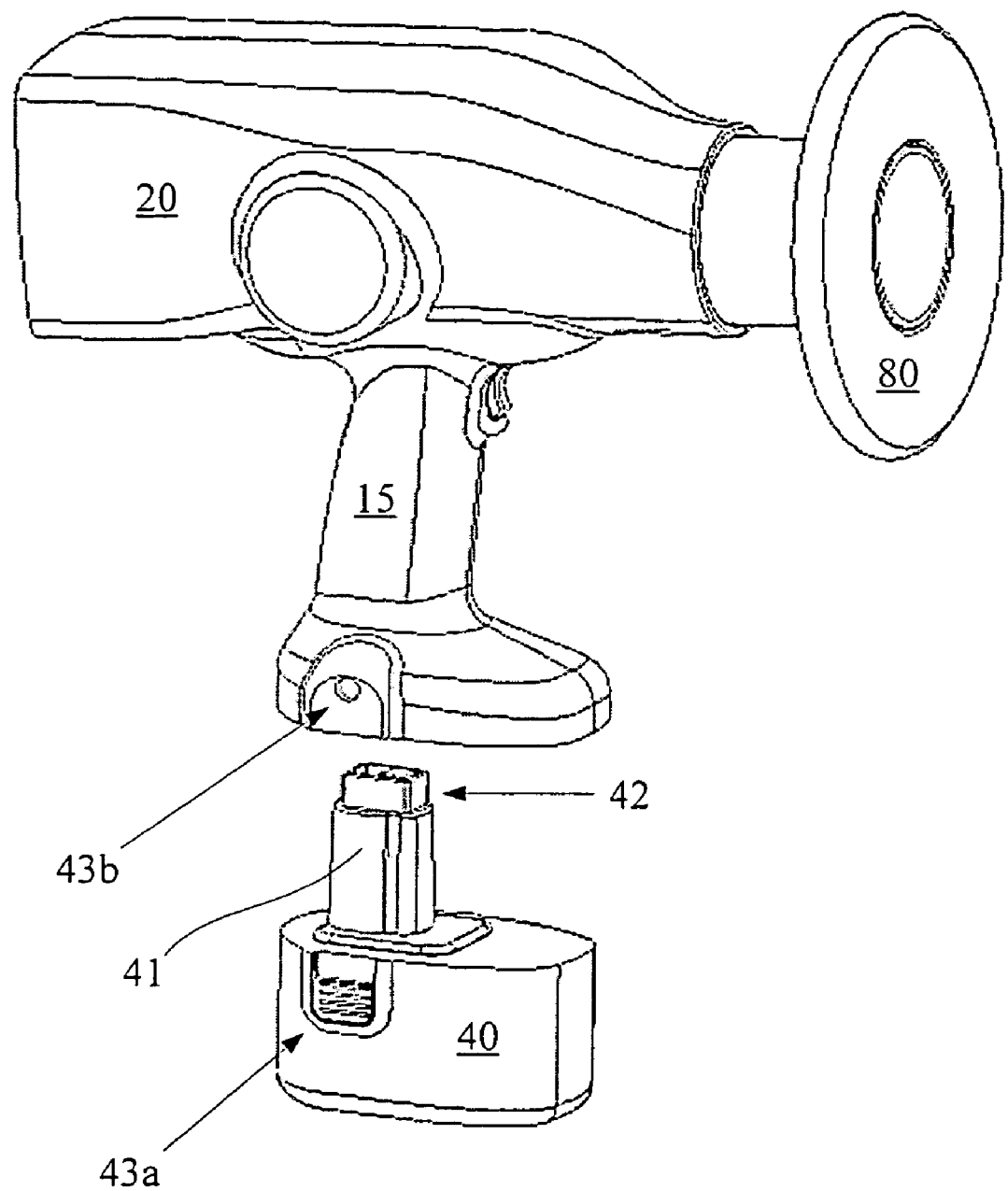

As shown in FIG. 7, the x-ray device 10 contains a locking mechanism 43b. To connect the power source 40 to the x-ray device 10, the power source 40 is gently pushed into the bottom of the handle 15 of the x-ray device 10. When completely connected, the electrical connector 42 connects with the internal electronics of the x-ray device 10. The locking mechanism 43b is automatically engaged to retain the power source 40 connected to the x-ray device 10 in this position. To remove the power source 40, the release mechanism 43a is actuated to unlock the locking mechanism 43b, and the power source 40 can be gently slid out from the handle 15.

The power source 40 is electrically connected to the conversion means using any connection means known in the art, including those described in the publications above. The conversion means converts the initial voltage supplied by the power source 40 to a converted voltage that is provided to the power supply 34. The conversion means generally converts the 14.4V (or similar voltage) provided by the power source 40 to a voltage ranging from about 80 to about 200V. In one aspect of the invention, the initial voltage is converted to a converted voltage of about 100V. Any conversion means known in the art that operates in this manner can be used in the invention, including the power management boards 36.

Figure 8:
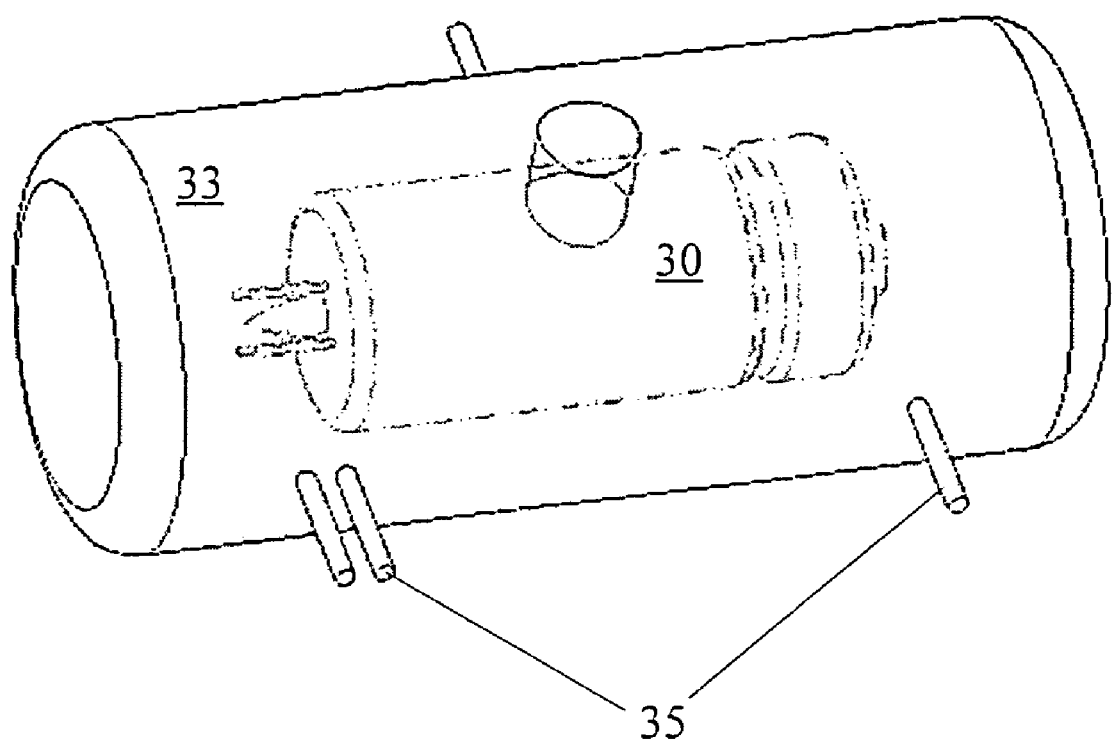
FIG. 8 depicts the x-ray tube of the x-ray device in one aspect of the invention.

The conversion means is electrically connected to the power supply 34. The power supply 34 steps up the converted voltage (i.e., the 100V) provided by the conversion means to a voltage that can be used by the x-ray tube 30. The power produced by the power supply 34 and input into the x-ray tube 30 via connection 35 (shown in FIG. 8) depends on the power needed to operate the x-ray tube, and the maximum power available from the power source. Generally, the power provided by the power supply 34 to the x-ray tube 30 can range from about 20 to about 150 kV. Typically, this power provided by the power supply can range from about 40 kV to about 100 kV.

Figure 5:
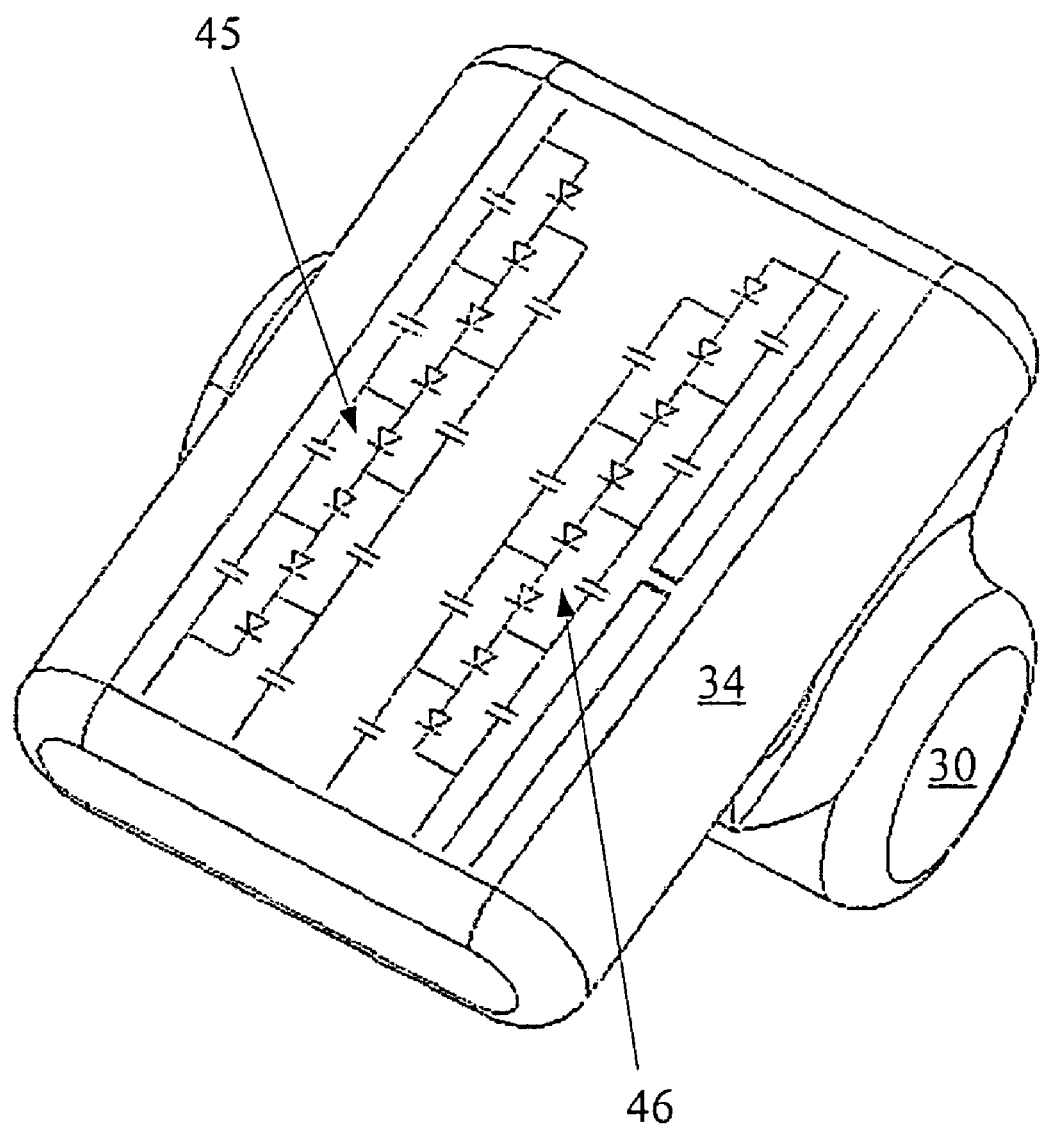
FIG. 5 depicts the x-ray tube and power supply of the x-ray device in one aspect of the invention.

In one aspect of the invention, the power provided by the power supply is provided by a plurality of individual power supplies. The number of individual power supplies used depends on the voltage needed for the x-ray tube, the space needed for the power supply 34, the total power available from the power source, and the number of electron-accelerating grids in the x-ray tube. In one aspect of the invention, the plurality of individual power supplies is two (as represented in FIG. 5 by 45, 46) where 45 supplies positive voltage to the anode and 46 supplies negative voltage to the cathode.

The power provided by each individual power supply depends on the number of individual power supplies used, the maximum power available from the power source, and the heat-dissipating capability of the x-ray tube. Generally, the power supplied by each individual power supply is the total power needed to operate the x-ray tube divided by the number of individual power supplies. For example, the power provided by each individual power supply (when there are 2) can range from about 20 kV to about 50 kV. In one aspect of the invention, the power provided by each individual power supply (when there are 2) is about +35 kV and −35 kV. In this embodiment, the +35 kV is attached to the anode of the x-ray tube and the −35 kV is attached to the cathode of the x-ray tube. A filament transformer is included in the cathode power supply to provide current to the x-ray tube filament and generate an electron beam at the cathode of the tube. The total power produced by the power supply is therefore the sum of the individual anode power supply and the individual cathode power supply.

Figure 9:
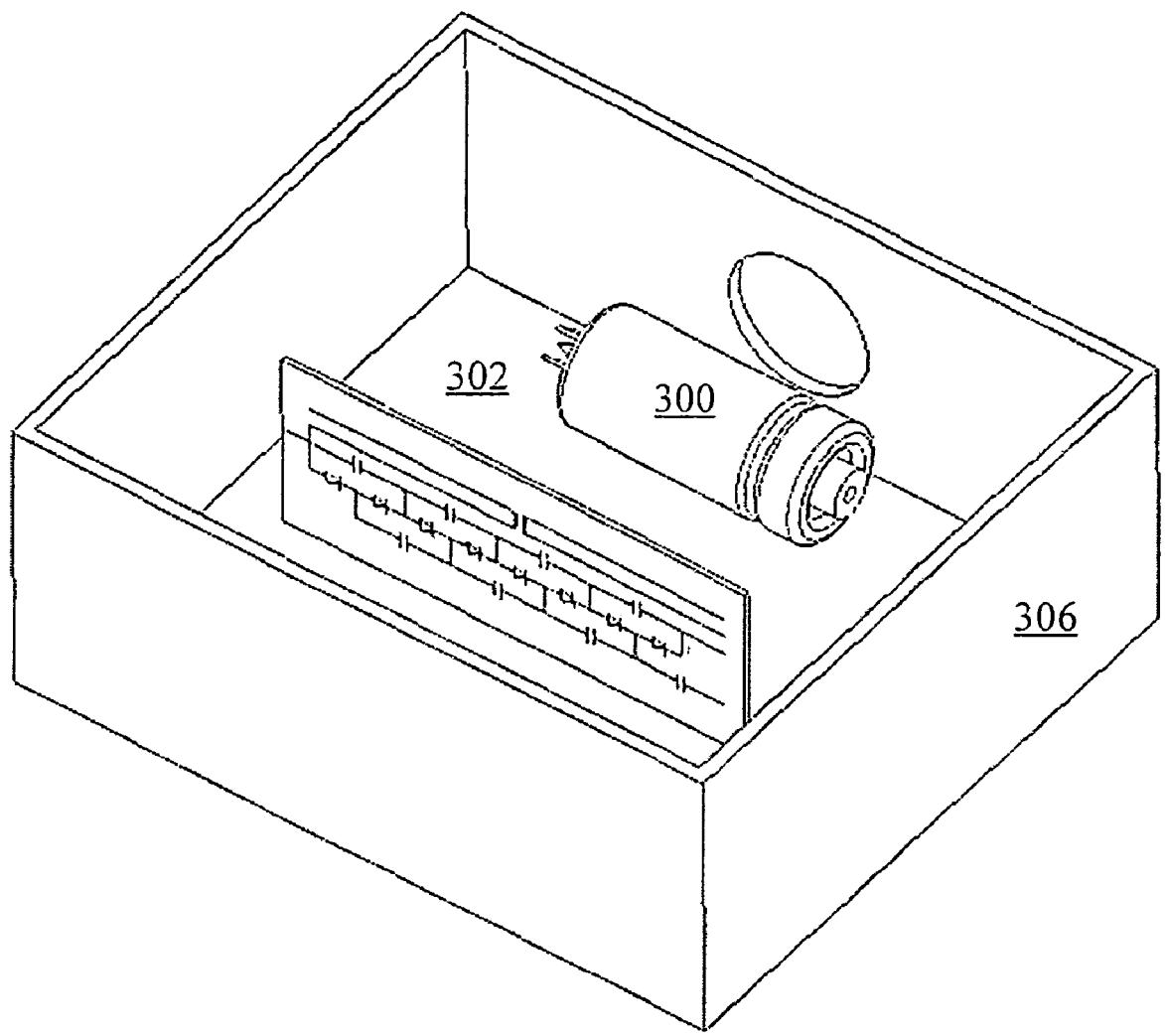
FIG. 9 depicts a conventional x-ray tube in a conventional configuration.

When such individual low voltage power supplies are used, the x-ray tube 30 of the invention becomes more portable. Conventional x-ray tubes operate at much higher voltages in the range of 70 kV and higher. Because of these high voltages, and the need for the high voltage standoff, the conventional x-ray tube 300 is often encased in insulating oil 302 (or a similar material) within a liquid-tight case 306 as shown in FIG. 9. The oil 302 also has the advantage of dissipating the high temperatures that existed during operation. By splitting the needed operation voltage into 2 (or more) individual power supplies, the individual power supplies only need to provide (and also stand off) half of the higher voltage.

With these lower voltages, the x-ray tube 30 of the invention can be encapsulated in materials other than high-density oil. These other materials need only insulate proportionately to the reduced voltage, i.e., these other materials need only insulate half as much as oil since the voltage produced is about half of that conventionally used. Any known material that can insulate in this manner can be used in the invention, including low-density materials like insulating gel, silicone rubber, epoxy, or combinations thereof. The insulating material is provided in a layer 33 that substantially encapsulates the x-ray tube 30 except for that portion of the tube where x-rays are actually emitted by the tube (i.e., into the x-ray collimator 32).

The thickness of the layer of insulating material 33 need only be sufficient for the purpose indicated above. Generally, the thickness of the insulating material can range from about ¼ inch to about 1 inch. In one aspect of the invention, such as where silicone rubber is used, the thickness of the insulating material can range from about ⅓ inch to about ½ inch. In another aspect of the invention, the insulating material comprises a dual-layer around the x-ray tube with the first layer comprising one of the insulating materials and the second layer comprising another of the insulating materials.

Eliminating the need to use the high-density oil provides a significant reduction in the weight of the unit. An added advantage is that there is no need for a liquid-tight case 306 to hold the liquid oil 302. Indeed, when a solid material is used such as silicone rubber, there is no need for any case, even though one can optionally be used. In one aspect of the invention by removing the case, and instead using silicon rubber that is conformal with the x-ray tube, the total volume of the insulating material is reduced significantly.

As shown in FIG. 9, conventional x-ray tubes 300 also contain a shielding to absorb stray x-rays that are emitted from the x-ray tube. The shielding usually was made of lead and incorporated into the liquid-tight case 306. Lead is conventionally used because of its excellent x-ray absorption properties. But lead shielding is quite heavy and consequently limits the portability of the x-ray device. With the x-ray device of the invention, this lead shielding has been eliminated, thereby increasing the portability by reducing the need for an additional component in the x-ray device. Instead, the insulating material (i.e., silicone rubber) has dispersed,within it a high-Z material. The high-Z material absorbs any stray x-rays that are emitted. Any high-Z material known in the art can be used, including compounds of Pb, W, Ta, Bi, Ba, or combinations thereof.

The concentration of the high-Z material in the insulating material need only be sufficient to absorb the expected amount of stray x-rays. Typically, the concentration of the high-Z material can range from about 30 wt % to about 60 wt %. In one aspect of the invention, the concentration of the high-Z material can range from about 45 wt % to about 50 wt %. In one aspect of the invention, the insulating material also contains substances that are known to optimize the thermal conductivity, such as metallic particles, or inclusions of high-thermal-conductivity materials.

The x-ray device of the invention optionally contains shielding 80 for the operator. When in operation, x-rays can often backscatter from the object being analyzed, such as the teeth of a patient, and strike the operator. The shielding 80 is used to protect the operator from such aberrant radiation. In one aspect of the invention, the shielding used is a Pb-filled acrylic radiation scatter shield.

Figure 3:
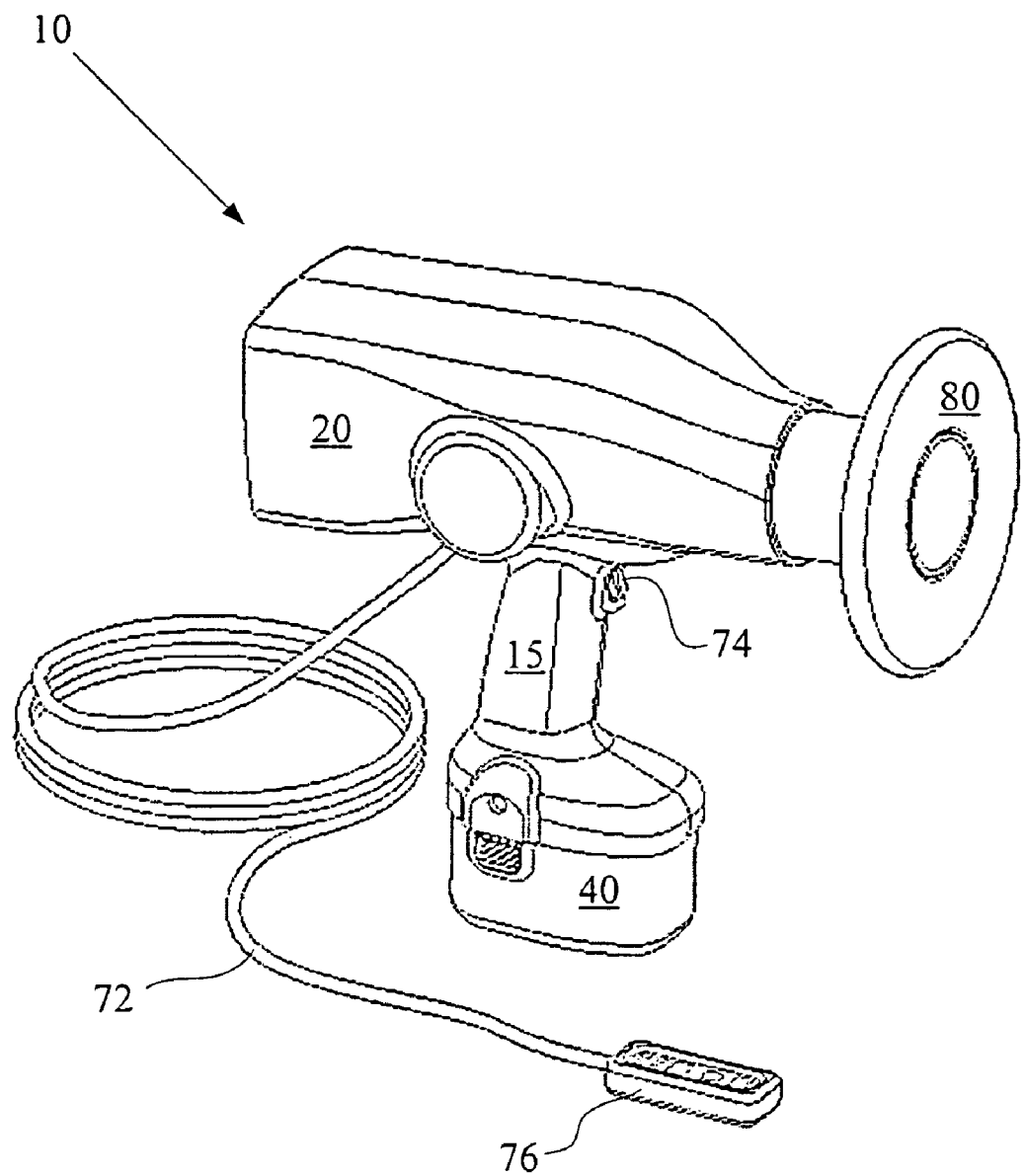
FIG. 3 depicts the x-ray device in another aspect of the invention.

The x-ray device of the invention also contains control means for operating the x-ray device. Any controls known in the art can be used in the control means of the invention. Examples of such controls include up and down arrow membrane switches with an LED readout to adjust exposure time. Indicators can include "power on," "start," and "x-rays on" LEDs. In the aspect of the invention illustrated in FIG. 1, the control means (controller 70) is integrated into the housing 20 of the device. In another aspect of the invention, the control means (such as controller 76) is external to the device and is connected to remainder of the device using any known electronic connection, such as cable 72 (See FIG. 3). In either instance, the control means also contains a trigger 74 that is incorporated into the handle 15 and used by the operator to begin (and conclude) the x-ray exposure.

Figure 10:
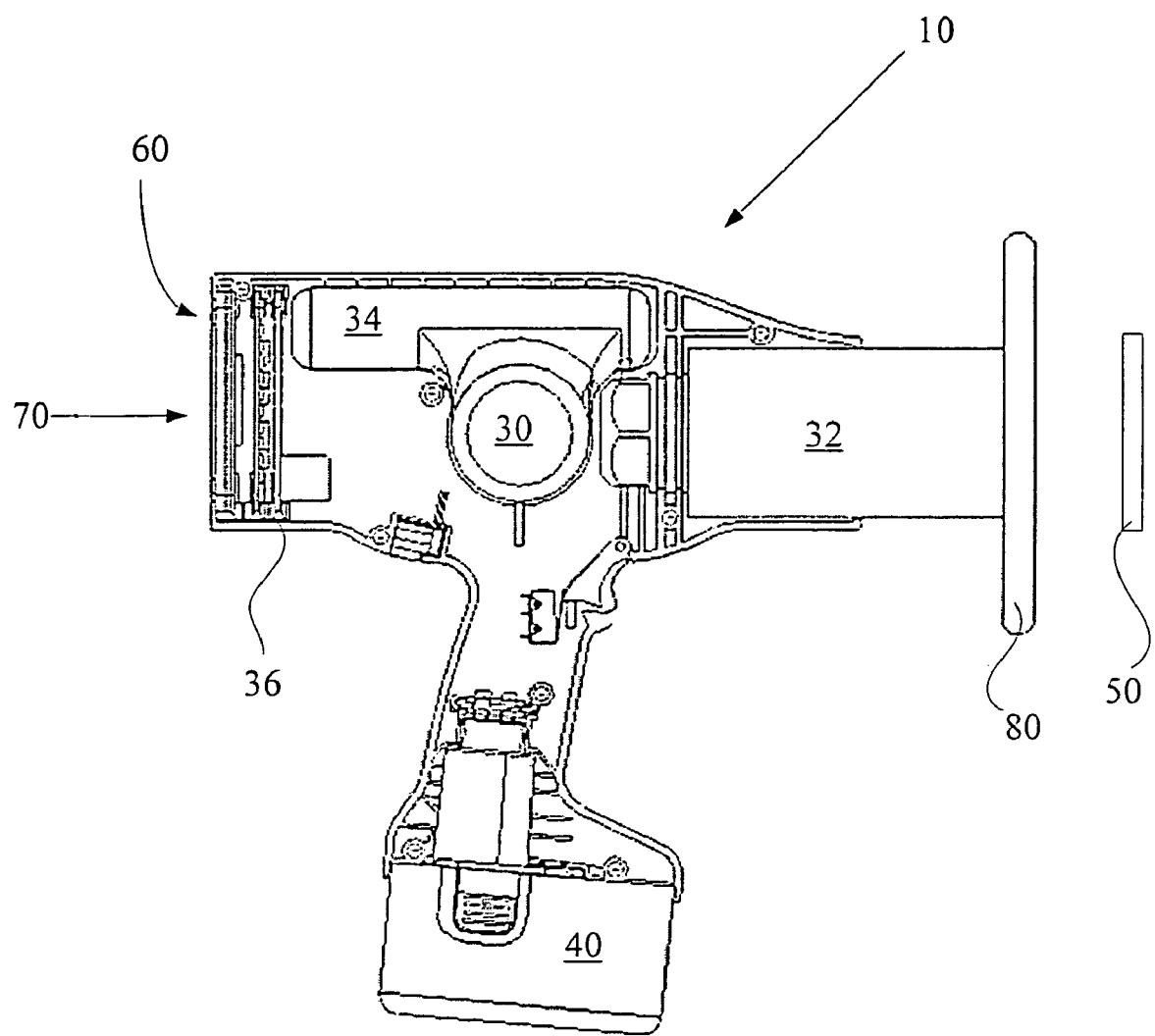
FIGS. 10-12 depicts the x-ray device in one aspect of the invention.

The invention also contains means for detecting or sensing the x-rays. Any detecting means known in the art that is sensitive to x-ray radiation can be used in the invention. Examples of such detecting means include x-rays receptors, x-ray film, CCD sensors, CMOS sensors, TFT sensors, imaging plates, and image intensifiers. In one aspect of the invention, and as illustrated in FIG. 10, a CCD sensor 50 is used as the detecting means in the x-ray devices of the invention.

The x-ray device may also contain means for displaying the x-rays detected by the detecting means. Any display means that displays the detected x-rays in a manner that can be understood by the operator of the device can be used for the invention. Examples of displaying means that can be used include film, imaging plates, and digital image displays such as cathode ray tubes (CRT) or liquid crystal display (LCD) screens. In one aspect of the invention, the display means can be used as a densitometer for the x-ray absorption.

In one aspect of the invention, the display means is integrated into the housing of the x-ray device. Such integration, however, will limit the size of the display means since too large a display means will detract from the portability of the device. In this aspect of the invention, any small display means with sufficient resolution can be used in the invention, including liquid crystal display (LCD) screens 60.

In another aspect of the invention, the display means are located external to the x-ray device. In this aspect, a separate imaging plate (such as a CMOS or TFT plate) for larger features (such as medical or veterinary imaging) can be used. The separate imaging plate can be connected to the remainder of the x-ray device as known in the art.

In one aspect of the invention, and as illustrated in FIG. 10, the x-ray device 10 can contain both a detecting means (such as CCD sensor 50), integrated display means (such as the LCD screen 60), and well as control means (such as controller 70). With these components, the size of the x-ray device can be minimized and the portability and uses of the x-ray device can be optimized.

The detecting means and the display means can be used to temporarily store images in the x-ray device. Once the storage capacity for these temporary images has been reached, an optional wired or wireless connection can then provide seamless update to an external electronic device or system, such as a permanent database or a desktop computer as known in the art. The wired or wireless connection can be made as known in the art. In one aspect of the invention, this connection is wireless since it provides true portability and freedom from line voltage.

In FIG. 10, the detecting means (CCD sensor 50) is not structurally attached to the x-ray device 10. Thus, in this aspect of the invention, the detecting means is free standing. With some of the known portable x-ray devices, the detecting means is structurally attached to the x-ray devices. Accordingly, the position of the detecting means is fixed relative to the rest of the x-ray device and when the x-ray device moves, so must the detecting means. This movement presents a problem for portable x-ray devices because any motion of the detecting means relative to the subject to be imaged result in distortion and blurring of the image. Because the detecting means of the invention is free-standing, any minor movements of the x-ray device of the invention will not result in distortion or blurring. As well, when the detecting means (i.e., a CCD sensor) is structurally attached, the x-ray device is typically configured to work with that specific type (e.g., size, shape) of the CCD sensor. The free-standing detecting means, however, can be interchanged with any given x-ray device without having to substantially modify the x-ray device.

In FIG. 10, the detecting means (i.e., CCD sensor 50) communicates with the x-ray device 10 by any known wireless transmission mechanism. Examples of some wireless transmission mechanisms include 802.11 protocols, wireless application protocols (WAP), Bluetooth® technology, or combinations thereof. In one aspect of the invention, Bluetooth® technology is used as the wireless transmission mechanism. The radiographic image detected by the detecting means (CCD sensor 50) is transmitted to the x-ray device 10 and then viewed via the display means 60.

The free-standing detecting means can be customized for analyzing any type of object. In one aspect of the invention, the CCD sensor can have non-flat configurations. In other aspects of the invention, the CCD sensor can have different types of shapes (other than the square illustrated in the Figures), such as rectangular, circular, oblong, polygonal, etc. . . . To achieve larger image areas, arrays of multiple detecting means can be assembled with electronics to resemble a single detecting means with the desired larger area.

Figure 11:
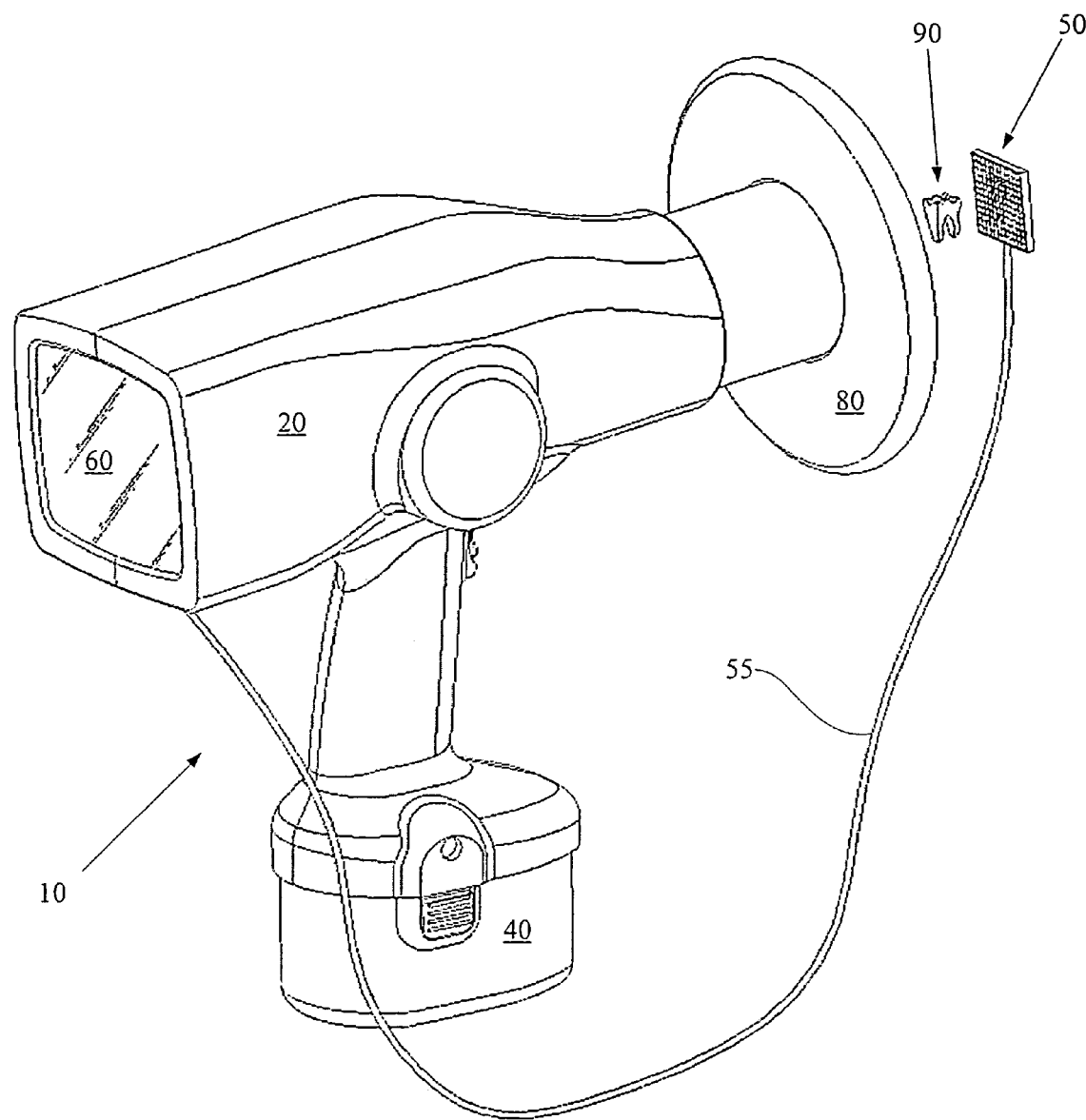
Figure 12:
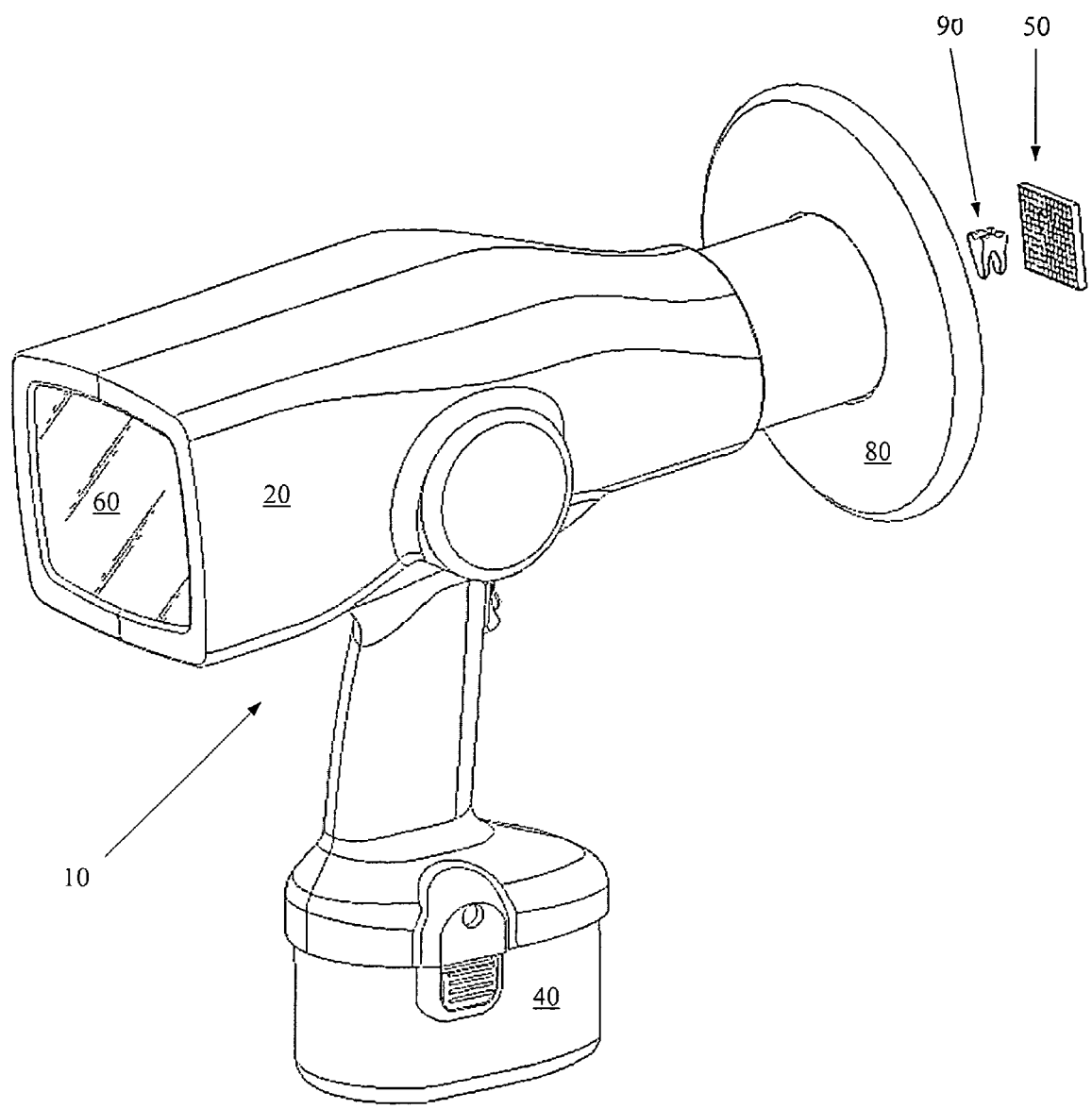
Figure 13:
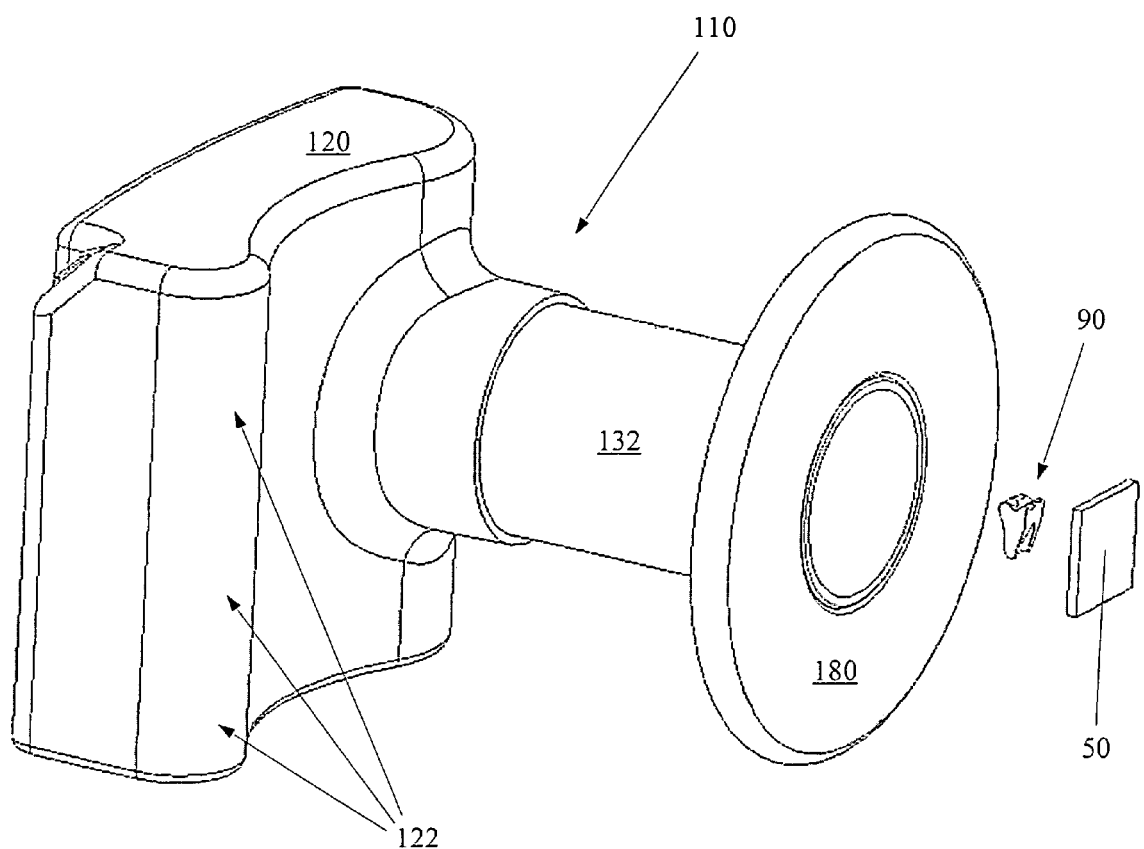
FIGS. 13-17 depicts the x-ray in another aspect of the invention.
Figure 14:
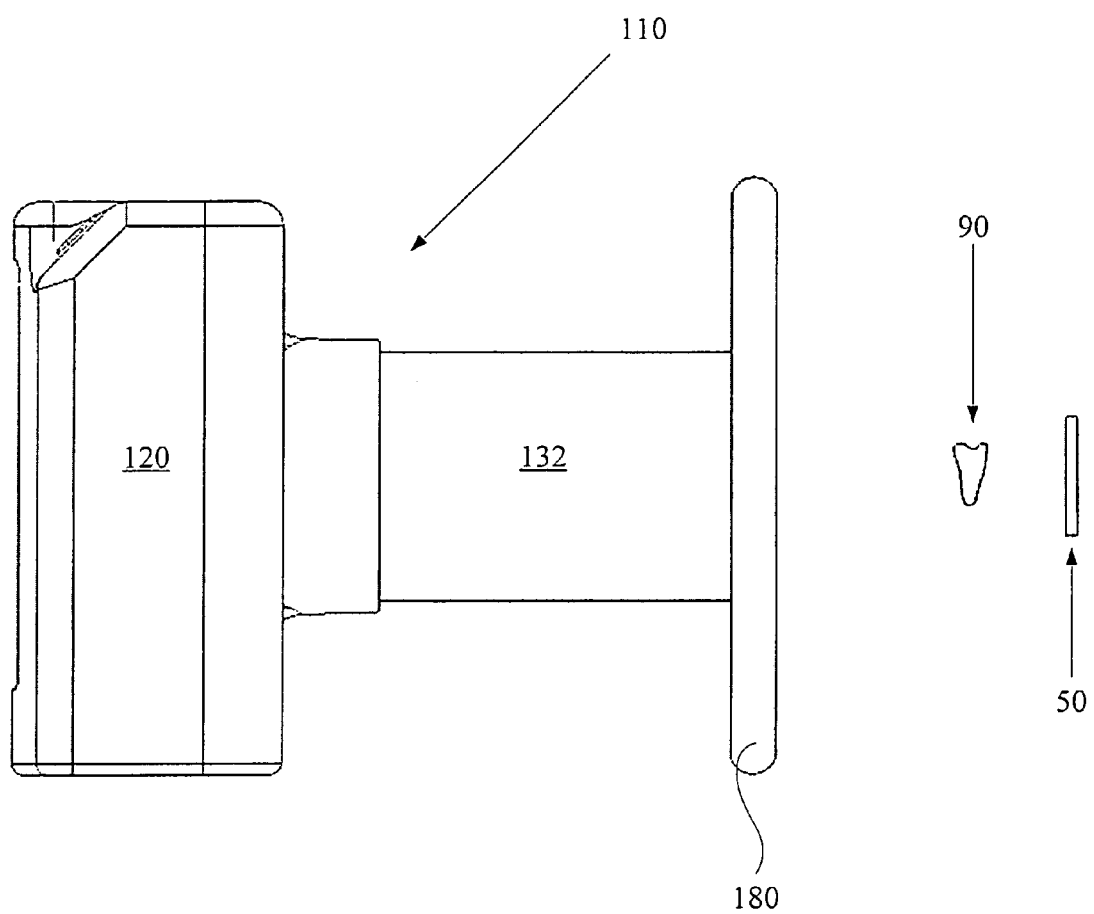
Figure 15:
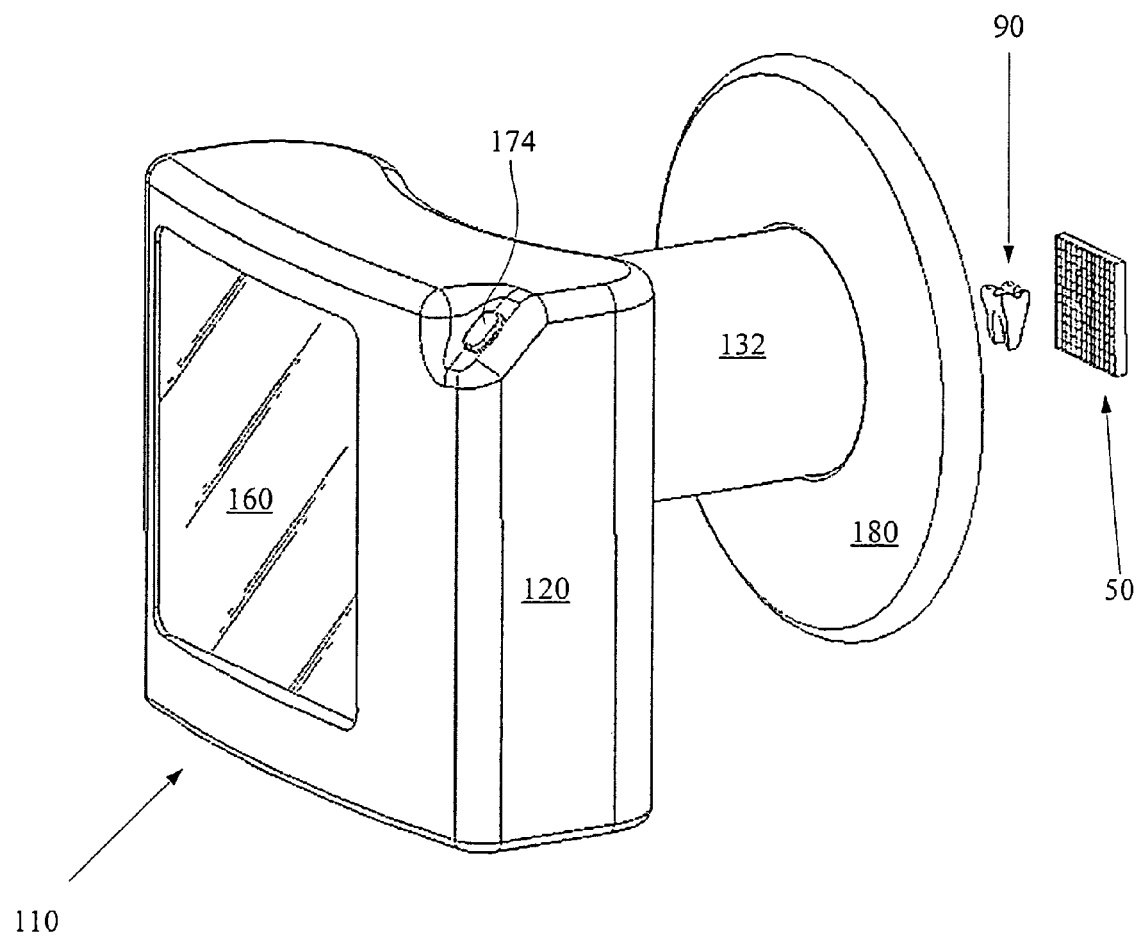

With the free-standing detecting means in this aspect of the invention, the x-ray device 10 is especially useful in the dental industry. As illustrated in FIG. 11, the x-ray device 10 can be used to analyze a tooth 90 (or multiple teeth) of a patient by placing the tooth 90 between the x-ray device 10 and the CCD sensor 50 and then operating the device. In FIG. 11, the CCD sensor 50 is connected to the x-ray device 10 by using any known wiring 55 (or cable) for that sensor to transmit the radiographic image to the x-ray device 10. A similar aspect of the invention is illustrated in FIG. 12, except that the wiring 55 has been replaced with wireless technology.

In a similar aspect of the invention, the x-ray device can be modified slightly to be used in medical industry. In this aspect of the invention, the size of the detecting means (i.e., CCD sensor or CMOS imaging plate) is increased to capture a larger radiographic image. The larger size would depend on the part of the body that is being analyzed, as well as the maximum field size of the x-ray device. Typically, the size of the detecting means can range up to about 24 inches. In one aspect of the invention, the size of the detecting means can range from about 10 to about 14 inches.

The x-ray device of the invention can also be configured differently in another aspect of the invention as shown in FIG. 13-16. In this aspect of the invention, the x-ray device 10 contains the same components as x-ray device 10, has been configured to look substantially like a traditional camera. This gives the impression to the operator of the x-ray device 10 that it operates like it looks: a camera, but for capturing digital radiological images.

As shown in FIG. 13-16, the x-ray device 10 contains housing 120 that is substantially rectangular in shape. In this aspect of the invention, the housing 120 does not contain a handle. Rather, the housing 120 can contain a protruding shape 122 that provides the operator with a better grip than a flat surface. Of course, the x-ray device 110 could contain similar features for the handling and operation of the device, such as texturing the surface for easier gripping or by providing indentations.

Like the x-ray device 10, the x-ray device 110 contains similar internal components such as an x-ray tube and an integrated power system. These internal components operate in substantially the same manner as x-ray device 10, but have been configured within the housing 120 to accommodate a different shape. As well, the x-ray device 110 contains control means (not shown), including trigger 174, radiation shielding 180, and any other components known in the art for efficient operation (such as x-ray collimator 132), including those components described in the documents mentioned above.

Figure 16:
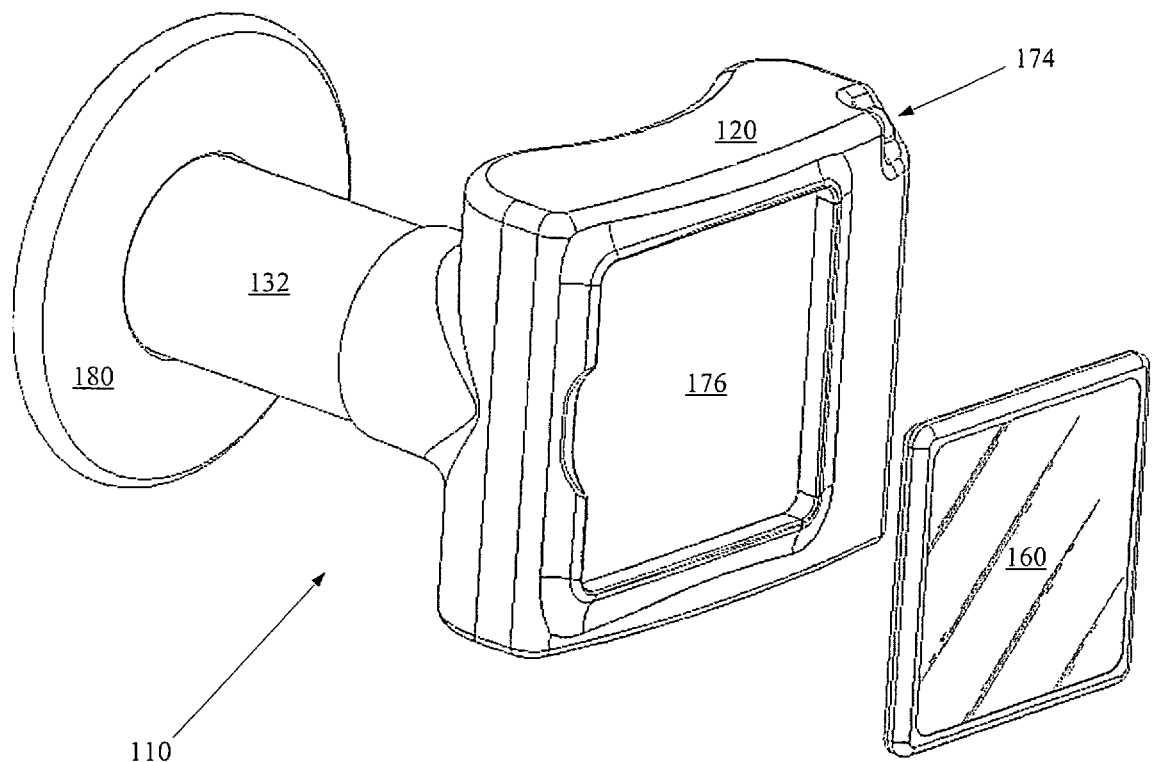

The x-ray device 110 also contains means for displaying the results of the analysis. In this aspect of the invention, the x-ray device 110 contains an integrated display means, like LCD screen 160. As shown in FIG. 16, the removeable LCD screen 160 is configured to fit easily within a hollow portion 176 in the rear of the device 110 where it can be easily viewed by the operator. Of course, external display means could also be used in the invention.

In one aspect of the invention, the display means and the control means are combined into a single means: a controllable display means. The controllable display means controls the operation of the x-ray device, as well as controls and manipulates the image display. The controllable display means can be either integrated into the x-ray device 110 or can be external to the x-ray device 110. Any controllable display means known in the art that operates in this manner can be used in the invention. One example of a controllable display means comprises a portable electronic device 165, such as a personal digital assistant (PDA), a handheld computer (like an iPAQ® Pocket PC), or a conventional camera-style LCD screen.

Using the portable electronic device with the x-ray device provides improved flexibility. For example, the portable electronic device—including both the hardware and the software—can be upgraded without needing to change the x-ray device itself. As well, the software in the portable electronic device can be used for image analysis, image enhancement, and for diagnosis at the point of image capture. Further, the x-ray device can be upgraded or modified with having to change the portable electronic device. Indeed, the portable electronic device could be customized so that any individual could take the customized settings and use them with any similar x-ray device.

Figure 17:
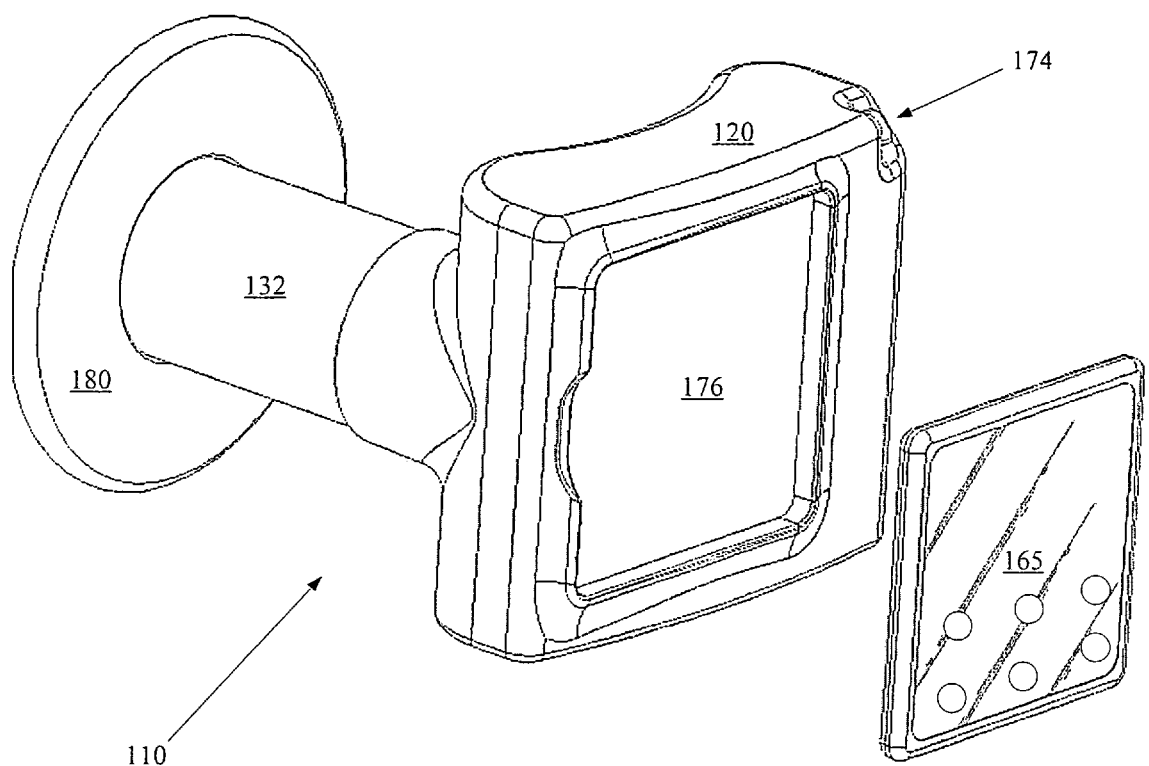

The controllable display means can be connected to the x-ray device 110 by wired or wireless technology. As shown in FIG. 17, the x-ray device 110 (including hollow portion 176) could be adapted to contain conventional interfaces in the hollow portion 176 for a portable electronic device 165.

Thus, the portable electronic device 165 is mechanically and electrically connected to the x-ray device when placed in hollow portion 176. As well, the portable electronic device 165 could be electrically connected to the x-ray device 110 using conventional wiring. Finally, the portable electronic device 165 could be remotely connected to the x-ray device using any conventional wireless technology.

Using the portable electronic device with the x-ray device 110 also increases the functionality of the x-ray device. For example, the portable electronic device could contain a temporary patient database. With flash memory storage devices, the patient database could be located on the portable electronic device and accessed when using the x-ray device. In another example, imaging software on the portable electronic device could allow for determining and manipulating features in the image, such as dental carries (cavities), breaks in bones, cracks in welds or pipes, identification of suspect shapes in security imaging, etc. . . .

Indeed, any function currently performed on a desktop computer or workstation could be performed right at the x-ray device, including contrast enhancement, image sharpening, smoothing, reverse shading, assignment of colors for different density materials, determination of relative densities,. etc. . . . All of these functions, as well as others, could be performed with the portable electronic device attached to the x-ray device, or with it operating remotely. The portable electronic device could then interface with any known external electronic device (such as a storage device, office computer, or workstation) using wired or wirelessly technology to transfer data and/or information. As well, the portable electronic device (and therefore the x-ray device) could utilize the additional capabilities provided by the external electronic device.

The x-ray devices of the invention can be made in any manner that provides the device with the components in this configuration described above. The housing, x-ray tube, detection means, display means, control means, radiation shielding, power source, and conversion means can be provided as known in the art and as described in the publications disclosed above. The insulating material can be made by mixing the needed amount of high-Z substance (such as an oxide of a heavy metal) into the insulating material (such as the silicone potting material when the A and B parts of the silicone are mixed together). The resulting combination is thoroughly mixed, and then uniformly provided around the x-ray tube, such as by pouring into an encapsulating mold. In this way, the insulating material containing the high-Z substance is uniformly distributed throughout the layer surrounding the x-ray tube.

When making the power supply, the process will be illustrated with two individual power supplies. Each power supply is configured so that the grounded ends of each power supply are located near the center of the x-ray tube. The positive voltage from one supply is provided to one side of the x-ray tube, and the negative voltage from the other supply is provided to other end of the x-ray tube. In this configuration, the maximum voltage (i.e., the sum of both) can be isolated from each individual power supply along the full length of the -x-ray tube and the isolation from ground only needs to be ½ of the total voltage. Consequently, the insulating paths need only be ½ the length.

The x-ray device can be operated in any manner that provides a radiographic image. In one aspect of the invention, the x-ray device 10 (or 110) of the invention can be operated by first actuating the appropriate button on the control means to turn on the device. After setting the exposure time, an "enable" button is pressed. This "enable" acts as a safety switch, preventing initiation of the x-ray exposure until the operator has positioned the instrument in the correct location and prepares to pull the trigger.

Then, on pulling the trigger (or pressing the "start" button) the high voltage (HV) supplied by the power supply 34 will increase up to about 70 kV (i.e., one power supply at about +35 kV and the other at about −35 kV). When this HV level is reached, the filament will energize at its full setpoint to supply the needed emission current to the x-ray tube. The filament will remain at this level for the time designated by the operator (i.e., by-using the controls). The start indicator in the LED of the control means can illuminate upon pressing the trigger. The "x-rays on" indicator in the LED of the control means can illuminate during the entire time that the emission current for the x-ray tube is present. Additionally, an audible signal can be used to indicate that the x-rays are being emitted.

During exposure after pressing the trigger 74 (or 174), x-rays are emitted from the x-ray tube 30 and strike the object being-analyzed, i.e., the teeth of a patient when the x-ray device is being used for dental purposes. To meet x-ray equipment standards, the button or trigger 74 (or 174) must be held down during the full length of the exposure. During exposure, the x-rays are used for analysis of the object as known in the art by using the detection means. The operator can then view the results of the analysis in the display means and optionally download the images to an external electronic device.

Following the exposure of a patient with the x-rays, the filament will turn off (along with the "x-rays on" indicator) and the HV will ramp down. Once the HV is off, the start indicator in the LED of the controller will turn off and the x-ray device will return to a standby condition. In one aspect of the invention, the operator may need to re-enter the exposure time before starting the next exposure. This re-entering process can be accomplished with a "ready." indicator in the LED of the control means after the exposure time has been set.

The x-ray device of the invention can be modified to contain additional optional features, including any of those described in the publications mentioned above. For example, to increase battery life, the x-ray device can contain an automatic shut off feature that shuts the device off after 2 minutes without an x-ray exposure. Another feature that can be added, for example, is to manufacture the housing or chassis 20 (or 120) of a high-impact material (such as ABS or a plastic alloy of ABS and other materials, designed for high-impact resistance) to reduce the risk of damage.

The x-ray device of the invention can also be made as part of a system for x-ray analysis. The system could contain any components that aid in the operation of the x-ray device or the x-ray analysis, including those mentioned above such as an external means for storing the radiographic images. As well, the system could also include a hard-side carrying case, an "industrial strength" tripod, a 3 meter long umbilical cord to a remote control panel 76, or the like. The system could also contain a back-up power source 40. Finally, the system could also contain any of those components described in the documents mentioned above.

Using the x-ray device of the invention provides several improvements over conventional devices. First, the x-ray device of the invention contains an integrated power system. The power system can be battery-operated, yet still provide a continuous high voltage, rather than Marx generators (pulsed) or capacitively-pulsed systems. Thus, the x-ray device can maintain a continuous DC high voltage supply and can generate a high voltage for a few seconds with each high current discharge. The high storage capacity provided by the batteries allows hundreds of discharges, anywhere from about 10 to about 20 amps for a few seconds. For most applications, including for dental purposes, the x-ray devices of the invention need less than a second for each exposure.

Most conventional x-ray devices, however, have external power supplies. Those conventional x-ray devices that do have integrated power supplies, still don't have the high current load described above. Thus, the power system of the invention can provide a constant radiation output and improved image quality while reducing the x-ray dosage to which the object (i.e., patient) is exposed.

Another improvement in the x-ray devices of the invention exists in the shielding for the x-ray tubes. Conventional x-ray tubes are shielded with a liquid oil encasement and lead shielding, both of which are bulky and heavy. Both of these components are eliminated in the x-ray tube shielding of the invention. Instead, the shielding of the invention contains a low-density insulating material that contains high-Z substances. This configuration leads to reduced material count and generally lower weight.

Other improvements result from the free-standing detecting means and the portable electronic device. With the free-standing detecting means, better images can be obtained even if the x-ray device moves. As well, the free-standing detecting means is more interchangeable with the x-ray device. When the portable electronic device is used with the x-ray device, the functionality (i.e., image display and manipulation) and interchangeability of the devices is greatly improved.

In addition to any previously indicated variation, numerous other modifications and alternative arrangements may be devised by those skilled in the art without departing from the spirit and scope of the invention and appended claims are intended to cover such modifications and arrangements. Thus, while the invention has been described above with particularity and detail in connection with what is presently deemed to be the most practical and preferred aspects of the invention, it will be apparent to those of ordinary skill in the art that numerous modifications, including but not limited to, form, function, manner of operation and use may be made without departing from the principles and concepts set forth herein.

What is claimed is:

1. A portable x-ray device, comprising:
   a housing containing an x-ray source and an integrated power system containing an internal power source;
   integrated display means comprising an LCD screen; and
   detecting means structurally unattached to the housing.

2. The device of claim 1, wherein the detecting means is electrically coupled to the x-ray device.

3. The device of claim 1, wherein the detecting means electrically communicates with the x-ray device using wireless technology.

4. The device of claim 1, wherein the device is a hand-held device.

5. The device of claim 1, wherein the device has a high current load for radiographic imaging.

6. The device of claim 1, wherein the power source can be removed from the housing.

7. The device of claim 1, wherein the power system comprises a plurality of power supplies with each power supply providing a power ranging from about 20 kV to about 50 kV.

8. The device of claim 1, wherein the x-ray source is shielded with a low-density insulating material containing a high-Z substance.

9. A hand-held x-ray device, comprising:
   a housing containing an x-ray source, an integrated power system containing an internal power source, and integrated display means comprising an LCD screen; and
   detecting means structurally unattached to the housing.

10. The device of claim 9, wherein the power source can be removed from the housing.

11. The device of claim 9, wherein the power system comprises a plurality of power supplies with each power supply providing a power ranging from about 20 kV to about 50 kV.

12. The device of claim 9, wherein the x-ray source is shielded with a low-density insulating material containing a high-Z substance.

13. A digital x-ray camera, comprising:
    a housing containing an x-ray source, an integrated power system containing an internal power source, and integrated display means comprising an LCD screen; and
    detecting means structurally unattached to the housing.

14. The camera of claim 13, wherein the power system comprises a plurality of power supplies with each power supply providing a power ranging from about 20 kV to about 50 kV.

15. The camera of claim 13, wherein the x-ray source is shielded with a low-density insulating material containing a high-Z substance.

16. A system for x-ray analysis, the system containing a digital x-ray camera with a housing containing an x-ray source, an integrated power system with an internal power source, and an integrated display means comprising an LCD screen, and detecting means structurally unattached to the housing.

17. The system of claim 16, wherein the power system comprises a plurality of power supplies with each power supply providing a power ranging from about 20 kV to about 50 kV.

18. The system of claim 16, wherein x-ray source is shielded with a low-density insulating material containing a high-Z substance.

19. A method for making a portable x-ray device, the method comprising:
    providing a housing with an x-ray source and an integrated power system containing an internal power source
    providing an integrated display means comprising an LCD screen; and
    providing detecting means structurally unattached to the housing.

20. The method of claim 19, including:
    providing the power system with a plurality of power supplies with each power supply providing a power ranging from about 20 kV to about 50 kV; and
    providing the x-ray source with a shielding comprising a low-density insulating material containing a high-Z substance.

21. A method for analysis, comprising:
    providing a digital x-ray camera with a housing containing an x-ray source, an integrated power system having an internal power source, and an integrated display means comprising an LCD screen, with detecting means structurally unattached to the housing; and
    powering the x-ray source using the integrated power system.

22. The method of claim 21, including:
providing the power system with a plurality of power supplies with each power supply providing a power ranging from about 20 kV to about 50 kV; and
providing the x-ray source with a shielding comprising a low-density insulating material containing a high-Z substance.

23. A method for dental imaging, comprising:
providing a digital x-ray camera with a housing containing an x-ray source, an integrated power system having an internal power source, and an integrated display means comprising an LCD screen, with detecting means structurally unattached to the housing; and
powering the x-ray source using the integrated power system so that x-rays impinge in the teeth of a patient.

24. The method of claim 23, including:
providing the power system with a plurality of power supplies with each power supply providing a power ranging from about 20 kV to about 50 kV; and
providing the x-ray source with a shielding comprising a low-density insulating material containing a high-Z substance.

25. The device of claim 1, further comprising a controllable display means.

26. The device of claim 25, wherein the controllable display means is integrated into the housing.

27. The device of claim 25, wherein the controllable display means is external to the x-ray device.

28. The device of claim 25, wherein the controllable display means comprises a portable electronic device.

29. The device of claim 9, wherein the device has a high current load for radiographic imaging.

30. A portable x-ray device, comprising:
a housing containing an x-ray source and an internal power source;
controllable display means integrated into the housing and comprising an LCD screen; and
detecting means structurally unattached to the housing.

31. The device of claim 30, wherein the device has a high current load for radiographic imaging.

32. The device of claim 30, wherein the x-ray source is located in a first portion of a housing and the internal power source is located in the second portion of the housing.

33. The device of claim 31, wherein the housing is configured for a user to hold the second portion and orient the first portion in the desired direction for emitting the x-rays.

* * * * *

(12) EX PARTE REEXAMINATION CERTIFICATE (10295th)
United States Patent
Turner

(10) Number: US 7,224,769 C1
(45) Certificate Issued: Sep. 12, 2014

(54) DIGITAL X-RAY CAMERA

(75) Inventor: D. Clark Turner, Payson, UT (US)

(73) Assignee: Aribex, Inc., Orem, UT (US)

Reexamination Request:
No. 90/012,436, Aug. 16, 2012

Reexamination Certificate for:
Patent No.: 7,224,769
Issued: May 29, 2007
Appl. No.: 10/529,806
Filed: Aug. 1, 2005

(21) Appl. No.: 90/012,436

(22) PCT Filed: Mar. 21, 2005

(86) PCT No.: PCT/US2005/005454
§ 371 (c)(1),
(2), (4) Date: Aug. 1, 2005

(87) PCT Pub. No.: WO2006/101468
PCT Pub. Date: Sep. 28, 2006

Related U.S. Application Data

(60) Provisional application No. 60/546,575, filed on Feb. 20, 2004.

(51) Int. Cl.
*H05G 1/64* (2006.01)
*H05G 1/10* (2006.01)

(52) U.S. Cl.
USPC .............................. 378/98.2; 378/98; 378/202

(58) Field of Classification Search
None
See application file for complete search history.

(56) References Cited

To view the complete listing of prior art documents cited during the proceeding for Reexamination Control Number 90/012,436, please refer to the USPTO's public Patent Application Information Retrieval (PAIR) system under the Display References tab.

*Primary Examiner* — Robert Nasser

(57) ABSTRACT

Portable x-ray devices and methods for using such devices are described. The devices have an x-ray tube powered by an integrated power system. The x-ray tube is shielded with a low-density insulating material containing a high-Z substance. The devices can also have an integrated display component. With these components, the size and weight of the x-ray devices can be reduced and the portability of the devices enhanced. The x-ray devices also have an x-ray detecting means that is not structurally attached to the device and therefore is free standing. Consequently, the x-ray devices can also be used as a digital x-ray camera. The portable x-ray devices are especially useful for applications where portability is an important feature such as in field work, remote operations, and mobile operations such as nursing homes, home healthcare, or teaching classrooms. This portability feature can be particularly useful in multi-suite medical and dental offices where a single x-ray device can be used as a digital x-ray camera in multiple offices instead of requiring a separate device in every office.

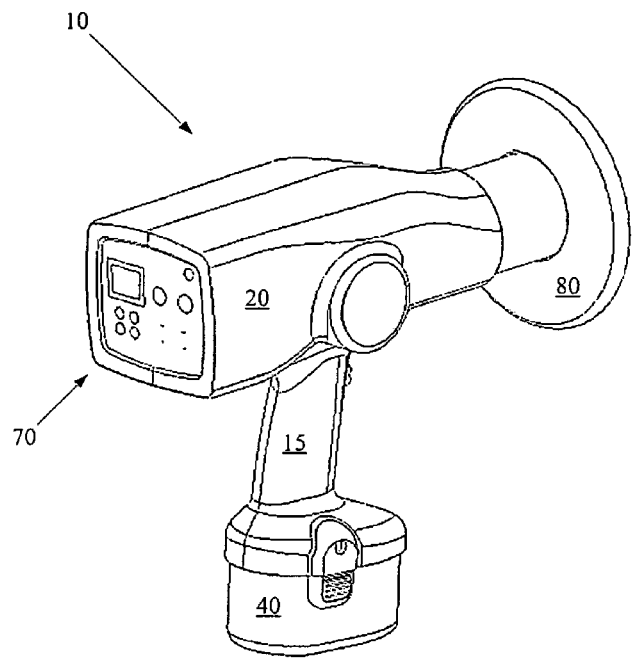

US 7,224,769 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-5, 7-9, 11-13, 15, 16, 18, 19, 21, 23 and 25-33 are cancelled.

Claims 6, 10, 14, 17, 20, 22 and 24 are determined to be patentable as amended.

New claims 34-64 are added and determined to be patentable.

6. [The device of claim 1,] *A portable x-ray device, comprising:*
a housing containing an x-ray source and an integrated power system containing an internal power source;
display means comprising an LCD screen integrated into the housing; and
detecting means structurally unattached to the housing;
wherein the power source can be removed from the housing.

10. [The device of claim 9,] *A hand-held x-ray device, comprising:*
*a housing containing an x-ray source, an integrated power system containing an internal power source, and display means comprising an LCD screen integrated into the housing; and*
*detecting means structurally unattached to the housing;*
wherein the power source can be removed from the housing.

14. [The camera of claim 13,] *A portable x-ray device, comprising:*
*a housing containing an x-ray source, an integrated power system containing an internal power source, and integrated display means comprising an LCD screen; and*
*detecting means structurally unattached to the housing;*
wherein the power system comprises a plurality of power supplies with each power supply providing a [power] *voltage* ranging from about 20 kV to about 50 kV.

17. [The system of claim 16,] *A system for x-ray analysis, the system containing a digital x-ray camera with a housing containing an x-ray source, an integrated power system with an internal power source, and an integrated display means comprising an LCD screen, and detecting means structurally unattached to the housing,*wherein the power system comprises a plurality of power supplies with each power supply providing a [power] *voltage* ranging from about 20 kV to about 50 kV.

20. [The method of claim 19, including] *A method for making a portable x-ray device, the method comprising:*
*providing a housing with an x-ray source and an integrated power system containing an internal power source providing an integrated display means comprising an LCD screen;*
*providing detecting means structurally unattached to the housing;*
providing the power system with a plurality of power supplies with each power supply providing a [power] *voltage* ranging from about 20 kV to about 50 kV; and
providing the x-ray source with a shielding comprising a low-density insulating material containing a high-Z substance.

22. [The method of claim 21, including:] *A method for analysis, comprising:*
*providing a digital x-ray camera with a housing containing an x-ray source, an integrated power system having an internal power source, and an integrated display means comprising an LCD screen, with detecting means structurally unattached to the housing;*
*powering the x-ray source using the integrated power system;*
providing the power system with a plurality of power supplies with each power supply providing a [power] *voltage* ranging from about 20 kV to about 50 kV; and
providing the x-ray source with a shielding comprising a low-density insulating material containing a high-Z substance.

24. [The method of claim 23, including:] *A method for dental imaging, comprising:*
*providing a digital x-ray camera with a housing containing an x-ray source, an integrated power system having an internal power source, and an integrated display means comprising an LCD screen, with detecting means structurally unattached to the housing;*
*powering the x-ray source using the integrated power system so that x-rays impinge in the teeth of a patient;*
providing the power system with a plurality of power supplies with each power supply providing a [power] *voltage* ranging from about 20 kV to about 50 kV; and
providing the x-ray source with a shielding comprising a low-density insulating material containing a high-Z substance.

*34. The device of claim 14, wherein the device is hand held during operation.*

*35. The device of claim 14, wherein the x-ray source is shielded with a low-density insulating material containing a high-Z substance.*

*36. The device of claim 14, wherein the integrated display means comprises a controllable display.*

*37. A hand held x-ray device, comprising:*
*a housing configured to be hand-held and containing an x-ray source, an integrated power system containing an internal power source, and integrated display means comprising an LCD screen, wherein the power system comprises a plurality of power supplies with each power supply providing a voltage ranging from about 20 kV to about 50 kV; and*
*detecting means structurally unattached to the housing.*

*38. The device of claim 37, wherein the x-ray source is shielded with a low-density insulating material containing a high-Z substance.*

*39. The device of claim 37, wherein the integrated display means comprises a controllable display.*

*40. The device of claim 37, wherein the integrated display means comprises a radiographic image display.*

*41. The system of claim 14, wherein the rower source can be removed from the housing.*

*42. A method for making a portable x-ray device, the method comprising:*
*providing a housing with an x-ray source and an integrated power system containing an internal power source providing an integrated display means comprising an LCD screen;* providing the power system with a plurality of power supplies with each power supply providing a voltage ranging from about 20 kV to about 50 kV for providing a continuous D.C. high voltage; and providing detecting means structurally unattached to the housing.

43. The method of claim 42, wherein the integrated display means is configured to display a radiographic image.

44. The method of claim 42, wherein the integrated display means comprises a controllable display.

45. A portable x-ray device, comprising:
    a housing containing an x-ray source and an integrated power system containing an internal power source;
    display means comprising an LCD screen integrated into the housing, the integrated display means configured to display a radiographic image; and
    detecting means structurally unattached to the housing.

46. The device of claim 45, wherein the radiographic image displayed comprises a medical image, a dental image, or a veterinary image.

47. A hand held x-ray device, comprising:
    a housing containing an x-ray source and an integrated power system containing an internal power source;
    radiographic image display means comprising an LCD screen integrated into the housing; and
    detecting means structurally unattached to the housing.

48. A portable x-ray device, comprising:
    a housing containing an x-ray source and an integrated power system containing an internal power source;
    controllable display means integrated into the housing and comprising an LCD screen, the display means configured to display a radiographic image; and
    detecting means structurally unattached to the housing.

49. A portable x-ray device, comprising:
    a housing containing an x-ray source and an integrated power system containing an internal power source;
    controllable display means integrated into the housing and comprising an LCD screen, the display means configured to display a radiographic image; and
    detecting means structurally unattached to the housing;
wherein a first portion of the housing encloses the power system and a second portion of the housing is removably attached to the first portion.

50. The device of claim 6, wherein the integrated display means comprises a radiographic image display.

51. The device of claim 10, wherein the integrated display means comprises a radiographic image display.

52. The device of claim 6, wherein the power system is configured to provide a continuous D.C. high voltage to the x-ray source.

53. The device of claim 10, wherein the display means is configured to display a radiographic image from x-rays being transmitted through a desired object.

54. The device of claim 49, further comprising:
    a shield configured to reduce backscatter radiation;
    wherein the integrated power system has a high current load suitable for medical or dental radiographic imaging, and is configured to provide a substantially constant x-ray radiation output;
    x-ray source shielding comprising a low-density insulating material containing a high-Z substance;
    wherein the display means contains a radiographic image display configured to display a medical image, a dental image, or a veterinary image from x-rays being transmitted through a desired object;
    wherein the device is configured to be hand held during operation; and
    wherein the power system is configured to provide a continuous D.C. high voltage to the x-ray source.

55. A portable x-ray device, comprising:
    a housing containing an x-ray source and an integrated power system containing an internal power source and an internal power supply;
    display means comprising an LCD screen integrated into the housing; and
    detecting means structurally unattached to the housing;
wherein the device has a high current load suitable for medical or dental radiographic imaging and wherein the high current load provides a substantially constant x-ray radiation output.

56. A portable x-ray device, comprising:
    a housing containing an x-ray source and an integrated power system containing an internal power source and an internal power supply;
    display means comprising an LCD screen, wherein the display means comprises a radiographic image display integrated into the housing; and
    detecting means structurally unattached to the housing.

57. The device of claim 56, wherein the radiographic image displayed comprises a medical image, a dental image, or a veterinary image.

58. A portable x-ray device, comprising:
    a housing containing an x-ray source and an integrated power system containing an internal power source and an internal power supply;
    display means comprising an LCD screen integrated into the housing; and
    detecting means structurally unattached to the housing;
wherein the power system is configured to provide a continuous D.C. high voltage to the x-ray source.

59. A portable x-ray device, comprising:
    a housing containing an x-ray source and an integrated power system containing an internal power source and an internal power supply;
    display means comprising an LCD screen integrated into the housing and configured to display a radiographic image from x-rays being transmitted through a desired object; and
    detecting means structurally unattached to the housing.

60. A portable x-ray device, comprising:
    a housing containing an x-ray source and an integrated power system containing an internal power source and an internal power supply;
    display means comprising an LCD screen integrated into the housing;
    detecting means structurally unattached to the housing;
    a shield configured to reduce backscatter radiation;
    wherein the integrated power system has a high current load suitable for medical or dental radiographic imaging and is configured to provide a substantially constant x-ray radiation output;
    wherein the device is configured to be hand held during operation; and
    wherein the power system is further configured to provide a continuous D.C. voltage ranging from about 20 kV to about 150 kV.

61. A portable x-ray device, comprising:
    a housing containing an x-ray source and an integrated power system containing an internal power source and an internal power supply;
    integrated display means comprising an LCD screen; and
    detecting means structurally unattached to the housing;

wherein the power system comprises a plurality of power supplies with each power supply providing a voltage ranging from about 20 kV to about 50 kV.

62. A method for analysis, comprising:
providing a digital x-ray camera with a housing containing an x-ray source, an integrated power system having an internal power source, and an integrated display means comprising an LCD screen, with detecting means structurally unattached to the housing;
powering the x-ray source using the integrated power system;
directing x-rays from the x-ray source toward a patient;
using the detecting means to detect x-rays passing through the patient;
generating a radiographic image based on the detected x-rays; and
displaying the radiographic image on the integrated display means.

63. The method of claim 62, including directing the x-rays toward the patient by holding the x-ray camera in a hand while the x-rays are emitted from the x-ray source.

64. The method of claim 62, further comprising locating the detecting means so that the x-rays pass through the teeth of the patient and impinge on the detecting means.

\* \* \* \* \*